United States Patent
Sowards et al.

(10) Patent No.: US 12,376,817 B2
(45) Date of Patent: Aug. 5, 2025

(54) OPTIMIZED FUNCTIONALITY THROUGH INTEROPERATION OF DOPPLER AND IMAGE BASED VESSEL DIFFERENTIATION

(71) Applicant: Bard Access Systems, Inc., Salt Lake City, UT (US)

(72) Inventors: Steffan Sowards, Salt Lake City, UT (US); Anthony K. Misener, Bountiful, UT (US); William Robert McLaughlin, Bountiful, UT (US)

(73) Assignee: Bard Access Systems, Inc., Salt Lake City, UT (US)

( * ) Notice: Subject to any disclaimer, the term of this patent is extended or adjusted under 35 U.S.C. 154(b) by 134 days.

(21) Appl. No.: 17/979,601

(22) Filed: Nov. 2, 2022

(65) Prior Publication Data
US 2023/0138970 A1    May 4, 2023

Related U.S. Application Data

(60) Provisional application No. 63/275,242, filed on Nov. 3, 2021.

(51) Int. Cl.
*A61B 8/06* (2006.01)
*A61B 8/00* (2006.01)
*A61B 8/08* (2006.01)

(52) U.S. Cl.
CPC .............. *A61B 8/06* (2013.01); *A61B 8/488* (2013.01); *A61B 8/0833* (2013.01)

(58) Field of Classification Search
CPC ......... A61B 5/489; A61B 8/0833; A61B 8/06; A61B 8/488; A61B 8/0891
See application file for complete search history.

(56) References Cited

U.S. PATENT DOCUMENTS

| 3,697,917 A | 10/1972 | Orth et al. |
| 5,148,809 A | 9/1992 | Biegeleisen-Knight et al. |

(Continued)

FOREIGN PATENT DOCUMENTS

| CN | 102871645 A | 1/2013 |
| CN | 105107067 B | 5/2018 |

(Continued)

OTHER PUBLICATIONS

U.S. Appl. No. 17/468,318, filed Sep. 7, 2021 Notice of Allowance dated Jan. 18, 2024.

(Continued)

*Primary Examiner* — Keith M Raymond
*Assistant Examiner* — Nyrobi Celestine
(74) *Attorney, Agent, or Firm* — Rutan & Tucker LLP

(57) ABSTRACT

An ultrasound-imaging system includes an ultrasound probe coupled with a console. Operations of the system can include detecting one or more blood vessels within the ultrasound image and identifying each blood vessel as a vein, an artery or other anatomic element using doppler ultrasound functionality of the ultrasound probe. Operations can also include determining a confidence for the blood vessel identification, and defining a window for doppler ultrasound operation. Operations can further include assessing a blood flow rate within blood vessels, and superimposing notifications atop the ultrasound image pertaining to the identity of the blood vessel including a confidence for the identity.

20 Claims, 8 Drawing Sheets

(56) References Cited

U.S. PATENT DOCUMENTS

| | | |
|---|---|---|
| 5,181,513 A | 1/1993 | Touboul et al. |
| 5,325,293 A | 6/1994 | Dorne |
| 5,349,865 A | 9/1994 | Kavli et al. |
| 5,441,052 A | 8/1995 | Miyajima |
| 5,549,554 A | 8/1996 | Miraki |
| 5,573,529 A | 11/1996 | Haak et al. |
| 5,758,650 A | 6/1998 | Miller et al. |
| 5,775,322 A | 7/1998 | Silverstein et al. |
| 5,879,297 A | 3/1999 | Haynor et al. |
| 5,897,503 A | 4/1999 | Lyon et al. |
| 5,908,387 A | 6/1999 | LeFree et al. |
| 5,967,984 A | 10/1999 | Chu et al. |
| 5,970,119 A | 10/1999 | Hofmann |
| 6,004,270 A | 12/1999 | Urbano et al. |
| 6,019,724 A | 2/2000 | Gronningsaeter et al. |
| 6,068,599 A | 5/2000 | Saito et al. |
| 6,074,367 A | 6/2000 | Hubbell |
| 6,129,668 A | 10/2000 | Haynor et al. |
| 6,132,379 A | 10/2000 | Patacsil et al. |
| 6,216,028 B1 | 4/2001 | Jaynor et al. |
| 6,233,476 B1 | 5/2001 | Strommer et al. |
| 6,245,018 B1 | 6/2001 | Lee |
| 6,263,230 B1 | 7/2001 | Haynor et al. |
| 6,375,615 B1 | 4/2002 | Flaherty et al. |
| 6,436,043 B2 | 8/2002 | Bonnefous |
| 6,498,942 B1 | 12/2002 | Esenaliev et al. |
| 6,503,205 B2 | 1/2003 | Manor et al. |
| 6,508,769 B2 | 1/2003 | Bonnefous |
| 6,511,458 B2 | 1/2003 | Milo et al. |
| 6,524,249 B2 | 2/2003 | Moehring et al. |
| 6,543,642 B1 | 4/2003 | Milliorn |
| 6,554,771 B1 | 4/2003 | Buil et al. |
| 6,592,520 B1 | 7/2003 | Peszynski et al. |
| 6,592,565 B2 | 7/2003 | Twardowski |
| 6,601,705 B2 | 8/2003 | Molina et al. |
| 6,612,992 B1 | 9/2003 | Hossack et al. |
| 6,613,002 B1 | 9/2003 | Clark et al. |
| 6,623,431 B1 | 9/2003 | Sakuma et al. |
| 6,641,538 B2 | 11/2003 | Nakaya et al. |
| 6,647,135 B2 | 11/2003 | Bonnefous |
| 6,687,386 B1 | 2/2004 | Ito et al. |
| 6,733,458 B1 | 5/2004 | Steins et al. |
| 6,749,569 B1 | 6/2004 | Pellegretti |
| 6,754,608 B2 | 6/2004 | Svanerudh et al. |
| 6,755,789 B2 | 6/2004 | Stringer et al. |
| 6,840,379 B2 | 1/2005 | Franks-Farah et al. |
| 6,857,196 B2 | 2/2005 | Dalrymple |
| 6,979,294 B1 | 12/2005 | Selzer et al. |
| 7,074,187 B2 | 7/2006 | Selzer et al. |
| 7,244,234 B2 | 7/2007 | Ridley et al. |
| 7,359,554 B2 | 4/2008 | Klingensmith et al. |
| 7,534,209 B2 | 5/2009 | Abend et al. |
| 7,599,730 B2 | 10/2009 | Hunter et al. |
| 7,637,870 B2 | 12/2009 | Flaherty et al. |
| 7,681,579 B2 | 3/2010 | Schwartz |
| 7,691,061 B2 | 4/2010 | Hirota |
| 7,699,779 B2 | 4/2010 | Sasaki et al. |
| 7,720,520 B2 | 5/2010 | Willis |
| 7,727,153 B2 | 6/2010 | Fritz et al. |
| 7,734,326 B2 | 6/2010 | Pedain et al. |
| 7,831,449 B2 | 11/2010 | Ying et al. |
| 7,905,837 B2 | 3/2011 | Suzuki |
| 7,925,327 B2 | 4/2011 | Weese |
| 7,927,278 B2 | 4/2011 | Selzer et al. |
| 8,014,848 B2 | 9/2011 | Birkenbach et al. |
| 8,038,619 B2 | 10/2011 | Steinbacher |
| 8,060,181 B2 | 11/2011 | Rodriguez Ponce et al. |
| 8,075,488 B2 | 12/2011 | Burton |
| 8,090,427 B2 | 1/2012 | Eck et al. |
| 8,105,239 B2 | 1/2012 | Specht |
| 8,172,754 B2 | 5/2012 | Watanabe et al. |
| 8,175,368 B2 | 5/2012 | Sathyanarayana |
| 8,200,313 B1 | 6/2012 | Rambod et al. |
| 8,211,023 B2 | 7/2012 | Swan et al. |
| 8,228,347 B2 | 7/2012 | Beasley et al. |
| 8,298,147 B2 | 10/2012 | Huennekens et al. |
| 8,303,505 B2 | 11/2012 | Webler et al. |
| 8,323,202 B2 | 12/2012 | Roschak et al. |
| 8,328,727 B2 | 12/2012 | Miele et al. |
| 8,336,536 B1 | 12/2012 | Wood-Putnam et al. |
| 8,388,541 B2 | 3/2013 | Messerly et al. |
| 8,409,103 B2 | 4/2013 | Grunwald et al. |
| 8,449,465 B2 | 5/2013 | Nair et al. |
| 8,553,954 B2 | 10/2013 | Saikia |
| 8,556,815 B2 | 10/2013 | Pelissier et al. |
| 8,585,600 B2 | 11/2013 | Liu et al. |
| 8,622,913 B2 | 1/2014 | Dentinger et al. |
| 8,706,457 B2 | 4/2014 | Hart et al. |
| 8,727,988 B2 | 5/2014 | Flaherty et al. |
| 8,734,357 B2 | 5/2014 | Taylor |
| 8,744,211 B2 | 6/2014 | Owen |
| 8,754,865 B2 | 6/2014 | Merritt et al. |
| 8,764,663 B2 | 7/2014 | Smok et al. |
| 8,781,194 B2 | 7/2014 | Malek et al. |
| 8,781,555 B2 | 7/2014 | Burnside et al. |
| 8,790,263 B2 | 7/2014 | Randall et al. |
| 8,849,382 B2 | 9/2014 | Cox et al. |
| 8,939,908 B2 | 1/2015 | Suzuki et al. |
| 8,961,420 B2 | 2/2015 | Zhang |
| 9,022,940 B2 | 5/2015 | Meier |
| 9,087,147 B1 | 7/2015 | Fonte |
| 9,138,290 B2 | 9/2015 | Hadjicostis |
| 9,199,082 B1 | 12/2015 | Yared et al. |
| 9,204,858 B2 | 12/2015 | Pelissier et al. |
| 9,220,477 B2 | 12/2015 | Urabe et al. |
| 9,295,447 B2 | 3/2016 | Shah |
| 9,320,493 B2 | 4/2016 | Visveshwara |
| 9,357,980 B2 | 6/2016 | Toji et al. |
| 9,364,171 B2 | 6/2016 | Harris et al. |
| 9,427,207 B2 | 8/2016 | Sheldon et al. |
| 9,445,780 B2 | 9/2016 | Hossack et al. |
| 9,456,766 B2 | 10/2016 | Cox et al. |
| 9,456,804 B2 | 10/2016 | Tamada |
| 9,468,413 B2 | 10/2016 | Hall et al. |
| 9,492,097 B2 | 11/2016 | Wilkes et al. |
| 9,521,961 B2 | 12/2016 | Silverstein et al. |
| 9,554,716 B2 | 1/2017 | Burnside et al. |
| 9,582,876 B2 | 2/2017 | Specht |
| 9,610,061 B2 | 4/2017 | Ebbini et al. |
| 9,636,031 B2 | 5/2017 | Cox |
| 9,649,037 B2 | 5/2017 | Lowe et al. |
| 9,649,048 B2 | 5/2017 | Cox et al. |
| 9,702,969 B2 | 7/2017 | Hope Simpson et al. |
| 9,715,757 B2 | 7/2017 | Ng et al. |
| 9,717,415 B2 | 8/2017 | Cohen et al. |
| 9,731,066 B2 | 8/2017 | Liu et al. |
| 9,814,433 B2 | 11/2017 | Benishti et al. |
| 9,814,531 B2 | 11/2017 | Yagi et al. |
| 9,861,337 B2 | 1/2018 | Patwardhan et al. |
| 9,895,138 B2 | 2/2018 | Sasaki |
| 9,913,605 B2 | 3/2018 | Harris et al. |
| 9,949,720 B2 | 4/2018 | Southard et al. |
| 10,043,272 B2 | 8/2018 | Forzoni et al. |
| 10,449,330 B2 | 10/2019 | Newman et al. |
| 10,524,691 B2 | 1/2020 | Newman et al. |
| 10,751,509 B2 | 8/2020 | Misener |
| 11,564,861 B1 | 1/2023 | Gaines |
| 11,900,593 B2 | 2/2024 | Dhatt et al. |
| 2002/0038088 A1 | 3/2002 | Imran et al. |
| 2003/0047126 A1 | 3/2003 | Tomaschko |
| 2003/0106825 A1 | 6/2003 | Molina et al. |
| 2003/0109910 A1 | 6/2003 | Lachenbruch et al. |
| 2003/0120154 A1 | 6/2003 | Sauer et al. |
| 2003/0125629 A1 | 7/2003 | Ustuner |
| 2003/0135115 A1 | 7/2003 | Burdette et al. |
| 2003/0149366 A1 | 8/2003 | Stringer et al. |
| 2003/0216648 A1 | 11/2003 | Lizzi et al. |
| 2004/0015080 A1 | 1/2004 | Kelly et al. |
| 2004/0055925 A1 | 3/2004 | Franks-Farah et al. |
| 2004/0197267 A1 | 10/2004 | Black et al. |
| 2005/0000975 A1 | 1/2005 | Carco et al. |
| 2005/0049504 A1 | 3/2005 | Lo et al. |
| 2005/0075597 A1 | 4/2005 | Vournakis et al. |
| 2005/0165299 A1 | 7/2005 | Kressy et al. |

(56) References Cited

U.S. PATENT DOCUMENTS

| | | |
|---|---|---|
| 2005/0251030 A1 | 11/2005 | Azar et al. |
| 2005/0267365 A1 | 12/2005 | Sokulin et al. |
| 2006/0004290 A1 | 1/2006 | Smith et al. |
| 2006/0013523 A1 | 1/2006 | Childers et al. |
| 2006/0015039 A1 | 1/2006 | Cassidy et al. |
| 2006/0020204 A1 | 1/2006 | Serra et al. |
| 2006/0047617 A1 | 3/2006 | Bacioiu et al. |
| 2006/0079781 A1 | 4/2006 | Germond-Rouet et al. |
| 2006/0184029 A1 | 8/2006 | Haim et al. |
| 2006/0210130 A1 | 9/2006 | Germond-Rouet et al. |
| 2006/0241463 A1* | 10/2006 | Shau ............... A61B 8/08 600/455 |
| 2007/0043341 A1 | 2/2007 | Anderson et al. |
| 2007/0049822 A1 | 3/2007 | Bunce et al. |
| 2007/0073155 A1 | 3/2007 | Park et al. |
| 2007/0167738 A1 | 7/2007 | Timinger et al. |
| 2007/0199848 A1 | 8/2007 | Ellswood et al. |
| 2007/0239005 A1 | 10/2007 | Ogasawara |
| 2007/0239120 A1 | 10/2007 | Brock et al. |
| 2007/0249911 A1 | 10/2007 | Simon |
| 2007/0287886 A1 | 12/2007 | Saadat |
| 2008/0021322 A1 | 1/2008 | Stone et al. |
| 2008/0033293 A1 | 2/2008 | Beasley et al. |
| 2008/0033759 A1 | 2/2008 | Finlay |
| 2008/0051657 A1 | 2/2008 | Rold |
| 2008/0108930 A1 | 5/2008 | Weitzel et al. |
| 2008/0125651 A1 | 5/2008 | Watanabe et al. |
| 2008/0146915 A1 | 6/2008 | McMorrow |
| 2008/0177186 A1 | 7/2008 | Slater et al. |
| 2008/0221425 A1 | 9/2008 | Olson et al. |
| 2008/0269605 A1* | 10/2008 | Nakaya ............... A61B 8/06 600/437 |
| 2008/0294037 A1 | 11/2008 | Richter |
| 2008/0300491 A1 | 12/2008 | Bonde et al. |
| 2009/0012399 A1 | 1/2009 | Sunagawa et al. |
| 2009/0012401 A1 | 1/2009 | Steinbacher |
| 2009/0074280 A1 | 3/2009 | Lu et al. |
| 2009/0105594 A1 | 4/2009 | Reynolds et al. |
| 2009/0124903 A1 | 5/2009 | Osaka |
| 2009/0137887 A1 | 5/2009 | Shariati et al. |
| 2009/0137907 A1 | 5/2009 | Takimoto et al. |
| 2009/0143672 A1 | 6/2009 | Harms et al. |
| 2009/0143684 A1 | 6/2009 | Cermak et al. |
| 2009/0156926 A1 | 6/2009 | Messerly et al. |
| 2009/0281413 A1 | 11/2009 | Boyden et al. |
| 2009/0306509 A1 | 12/2009 | Pedersen et al. |
| 2010/0010348 A1 | 1/2010 | Halmann |
| 2010/0168576 A1 | 7/2010 | Poland et al. |
| 2010/0211026 A2 | 8/2010 | Sheetz et al. |
| 2010/0249598 A1 | 9/2010 | Smith et al. |
| 2010/0286515 A1 | 11/2010 | Gravenstein et al. |
| 2010/0312121 A1 | 12/2010 | Guan |
| 2010/0324423 A1 | 12/2010 | El-Aklouk et al. |
| 2011/0002518 A1 | 1/2011 | Ziv-Ari et al. |
| 2011/0026796 A1 | 2/2011 | Hyun et al. |
| 2011/0071404 A1 | 3/2011 | Schmitt et al. |
| 2011/0074244 A1 | 3/2011 | Osawa |
| 2011/0087107 A1 | 4/2011 | Lindekugel et al. |
| 2011/0166451 A1 | 7/2011 | Blaivas et al. |
| 2011/0282188 A1 | 11/2011 | Burnside et al. |
| 2011/0295108 A1 | 12/2011 | Cox et al. |
| 2011/0313293 A1 | 12/2011 | Lindekugel et al. |
| 2012/0136242 A1 | 5/2012 | Qi et al. |
| 2012/0136256 A1 | 5/2012 | Nozaki et al. |
| 2012/0165679 A1 | 6/2012 | Orome et al. |
| 2012/0179038 A1 | 7/2012 | Meurer et al. |
| 2012/0179042 A1 | 7/2012 | Fukumoto et al. |
| 2012/0179044 A1 | 7/2012 | Chiang et al. |
| 2012/0197132 A1 | 8/2012 | O'Connor |
| 2012/0220865 A1 | 8/2012 | Brown et al. |
| 2012/0277576 A1 | 11/2012 | Lui |
| 2013/0041250 A1* | 2/2013 | Pelissier ............... A61B 8/461 600/424 |
| 2013/0102889 A1 | 4/2013 | Southard et al. |
| 2013/0131499 A1 | 5/2013 | Chan et al. |
| 2013/0131502 A1 | 5/2013 | Blaivas et al. |
| 2013/0144166 A1 | 6/2013 | Specht et al. |
| 2013/0150724 A1 | 6/2013 | Blaivas et al. |
| 2013/0188832 A1 | 7/2013 | Ma et al. |
| 2013/0197367 A1 | 8/2013 | Smok et al. |
| 2013/0218024 A1 | 8/2013 | Boctor et al. |
| 2013/0323700 A1 | 12/2013 | Samosky et al. |
| 2013/0338503 A1 | 12/2013 | Cohen et al. |
| 2013/0338508 A1 | 12/2013 | Nakamura et al. |
| 2013/0345566 A1* | 12/2013 | Weitzel ............... A61B 8/4427 600/443 |
| 2014/0005530 A1 | 1/2014 | Liu et al. |
| 2014/0031694 A1 | 1/2014 | Solek |
| 2014/0066779 A1 | 3/2014 | Nakanishi |
| 2014/0073976 A1 | 3/2014 | Fonte et al. |
| 2014/0100440 A1 | 4/2014 | Cheline et al. |
| 2014/0114194 A1 | 4/2014 | Kanayama et al. |
| 2014/0170620 A1 | 6/2014 | Savitsky et al. |
| 2014/0180098 A1 | 6/2014 | Flaherty et al. |
| 2014/0180116 A1 | 6/2014 | Lindekugel et al. |
| 2014/0188133 A1 | 7/2014 | Misener |
| 2014/0188440 A1 | 7/2014 | Donhowe et al. |
| 2014/0276059 A1 | 9/2014 | Sheehan |
| 2014/0276069 A1 | 9/2014 | Amble et al. |
| 2014/0276081 A1 | 9/2014 | Tegels |
| 2014/0276085 A1 | 9/2014 | Miller |
| 2014/0276690 A1 | 9/2014 | Grace |
| 2014/0296694 A1 | 10/2014 | Jaworski |
| 2014/0343431 A1 | 11/2014 | Vajinepalli et al. |
| 2014/0357994 A1 | 12/2014 | Jin et al. |
| 2015/0005738 A1 | 1/2015 | Blacker |
| 2015/0011887 A1 | 1/2015 | Ahn et al. |
| 2015/0065916 A1 | 3/2015 | Maguire et al. |
| 2015/0073279 A1 | 3/2015 | Cai et al. |
| 2015/0112200 A1 | 4/2015 | Oberg et al. |
| 2015/0141821 A1 | 5/2015 | Yoshikawa et al. |
| 2015/0190111 A1* | 7/2015 | Fry ............... A61B 8/4209 600/438 |
| 2015/0209003 A1 | 7/2015 | Halmann et al. |
| 2015/0209113 A1 | 7/2015 | Burkholz et al. |
| 2015/0209510 A1 | 7/2015 | Burkholz et al. |
| 2015/0209526 A1 | 7/2015 | Matsubara et al. |
| 2015/0245820 A1* | 9/2015 | Tamada ............... G16H 50/30 600/449 |
| 2015/0257735 A1 | 9/2015 | Ball et al. |
| 2015/0272448 A1 | 10/2015 | Fonte et al. |
| 2015/0282890 A1 | 10/2015 | Cohen et al. |
| 2015/0294497 A1* | 10/2015 | Ng ............... A61B 8/0891 382/128 |
| 2015/0297097 A1 | 10/2015 | Matsubara et al. |
| 2015/0342572 A1 | 12/2015 | Tahmasebi Maraghoosh et al. |
| 2015/0359520 A1 | 12/2015 | Shan et al. |
| 2015/0359991 A1 | 12/2015 | Dunbar et al. |
| 2016/0000367 A1 | 1/2016 | Lyon |
| 2016/0000399 A1 | 1/2016 | Halmann et al. |
| 2016/0026894 A1 | 1/2016 | Nagase |
| 2016/0029995 A1 | 2/2016 | Navratil et al. |
| 2016/0038119 A1 | 2/2016 | Desjardins |
| 2016/0081674 A1 | 3/2016 | Bagwan et al. |
| 2016/0113517 A1 | 4/2016 | Lee et al. |
| 2016/0113699 A1 | 4/2016 | Sverdlik et al. |
| 2016/0120607 A1 | 5/2016 | Sorotzkin et al. |
| 2016/0125639 A1 | 5/2016 | Park et al. |
| 2016/0157831 A1 | 6/2016 | Kang et al. |
| 2016/0166232 A1 | 6/2016 | Merritt |
| 2016/0202053 A1 | 7/2016 | Walker et al. |
| 2016/0211045 A1 | 7/2016 | Jeon et al. |
| 2016/0213398 A1 | 7/2016 | Liu |
| 2016/0220124 A1 | 8/2016 | Grady et al. |
| 2016/0259992 A1 | 9/2016 | Knodt et al. |
| 2016/0278869 A1 | 9/2016 | Grunwald |
| 2016/0287214 A1 | 10/2016 | Ralovich et al. |
| 2016/0296208 A1 | 10/2016 | Sethuraman et al. |
| 2016/0374644 A1 | 12/2016 | Mauldin, Jr. et al. |
| 2017/0014105 A1* | 1/2017 | Chono ............... A61B 8/14 |
| 2017/0020561 A1 | 1/2017 | Cox et al. |
| 2017/0079548 A1 | 3/2017 | Silverstein et al. |
| 2017/0086785 A1 | 3/2017 | Bjaerum |
| 2017/0090571 A1 | 3/2017 | Bjaerum et al. |

(56) References Cited

U.S. PATENT DOCUMENTS

| | | |
|---|---|---|
| 2017/0103534 A1 | 4/2017 | Park et al. |
| 2017/0143312 A1 | 5/2017 | Hedlund et al. |
| 2017/0164923 A1 | 6/2017 | Matsumoto |
| 2017/0172666 A1 | 6/2017 | Govari et al. |
| 2017/0215842 A1 | 8/2017 | Ryu et al. |
| 2017/0252004 A1 | 9/2017 | Broad et al. |
| 2017/0258522 A1 | 9/2017 | Goshgarian et al. |
| 2017/0328751 A1 | 11/2017 | Lemke |
| 2017/0367678 A1 | 12/2017 | Sirtori et al. |
| 2018/0015256 A1 | 1/2018 | Southard et al. |
| 2018/0116723 A1 | 5/2018 | Hettrick et al. |
| 2018/0125450 A1 | 5/2018 | Blackbourne et al. |
| 2018/0161502 A1 | 6/2018 | Nanan et al. |
| 2018/0199914 A1 | 7/2018 | Ramachandran et al. |
| 2018/0214119 A1 | 8/2018 | Mehrmohammadi et al. |
| 2018/0228465 A1 | 8/2018 | Southard et al. |
| 2018/0235649 A1 | 8/2018 | Elkadi |
| 2018/0235709 A1 | 8/2018 | Donhowe et al. |
| 2018/0289927 A1 | 10/2018 | Messerly |
| 2018/0296185 A1 | 10/2018 | Cox et al. |
| 2018/0310955 A1 | 11/2018 | Lindekugel et al. |
| 2018/0333135 A1 | 11/2018 | Kim et al. |
| 2018/0344293 A1 | 12/2018 | Raju et al. |
| 2019/0029636 A1 | 1/2019 | Lee et al. |
| 2019/0060001 A1 | 2/2019 | Kohli et al. |
| 2019/0060014 A1 | 2/2019 | Hazelton et al. |
| 2019/0090855 A1 | 3/2019 | Kobayashi et al. |
| 2019/0125210 A1 | 5/2019 | Govari et al. |
| 2019/0200951 A1 | 7/2019 | Meier |
| 2019/0239848 A1 | 8/2019 | Bedi et al. |
| 2019/0239850 A1 | 8/2019 | Dalvin et al. |
| 2019/0307419 A1 | 10/2019 | Durfee |
| 2019/0307515 A1 | 10/2019 | Naito et al. |
| 2019/0307516 A1 | 10/2019 | Schotzko et al. |
| 2019/0365347 A1 | 12/2019 | Abe |
| 2019/0365348 A1 | 12/2019 | Toume et al. |
| 2019/0365354 A1 | 12/2019 | Du |
| 2020/0069929 A1 | 3/2020 | Mason et al. |
| 2020/0107596 A1 | 4/2020 | Caruso et al. |
| 2020/0113540 A1 | 4/2020 | Gijsbers et al. |
| 2020/0163654 A1 | 5/2020 | Satir et al. |
| 2020/0200900 A1 | 6/2020 | Asami et al. |
| 2020/0229795 A1* | 7/2020 | Tadross .................. A61B 8/54 |
| 2020/0230391 A1 | 7/2020 | Burkholz et al. |
| 2020/0237403 A1 | 7/2020 | Southard et al. |
| 2020/0281563 A1 | 9/2020 | Muller et al. |
| 2020/0359990 A1 | 11/2020 | Poland et al. |
| 2020/0390416 A1 | 12/2020 | Swan et al. |
| 2021/0045716 A1 | 2/2021 | Shiran et al. |
| 2021/0059639 A1 | 3/2021 | Howell |
| 2021/0077058 A1* | 3/2021 | Mashood ............... A61B 8/429 |
| 2021/0137492 A1* | 5/2021 | Imai ..................... A61B 8/4254 |
| 2021/0146167 A1 | 5/2021 | Barthe et al. |
| 2021/0161510 A1 | 6/2021 | Sasaki et al. |
| 2021/0186467 A1 | 6/2021 | Urabe et al. |
| 2021/0212658 A1 | 7/2021 | McGrath et al. |
| 2021/0212668 A1 | 7/2021 | Li et al. |
| 2021/0267569 A1 | 9/2021 | Yamamoto |
| 2021/0267570 A1 | 9/2021 | Ulman et al. |
| 2021/0295048 A1* | 9/2021 | Buras .................... G06N 20/00 |
| 2021/0315538 A1 | 10/2021 | Brandl et al. |
| 2021/0373602 A1 | 12/2021 | Min |
| 2021/0378627 A1* | 12/2021 | Yarmush ............. A61B 8/4218 |
| 2022/0019313 A1* | 1/2022 | He ......................... G01F 1/662 |
| 2022/0022969 A1 | 1/2022 | Misener |
| 2022/0039777 A1 | 2/2022 | Durfee |
| 2022/0039829 A1 | 2/2022 | Zijlstra et al. |
| 2022/0071593 A1 | 3/2022 | Tran |
| 2022/0096053 A1* | 3/2022 | Sethuraman ......... A61B 8/5207 |
| 2022/0096797 A1 | 3/2022 | Prince |
| 2022/0104791 A1 | 4/2022 | Matsumoto |
| 2022/0104886 A1 | 4/2022 | Blanchard et al. |
| 2022/0117582 A1 | 4/2022 | McLaughlin et al. |
| 2022/0160434 A1 | 5/2022 | Messerly et al. |
| 2022/0168050 A1 | 6/2022 | Sowards et al. |
| 2022/0172354 A1 | 6/2022 | Misener et al. |
| 2022/0225963 A1 | 7/2022 | Sutton et al. |
| 2022/0233346 A1 | 7/2022 | McElya |
| 2022/0296303 A1* | 9/2022 | McLeod ............... G06T 7/0012 |
| 2022/0304652 A1 | 9/2022 | Peterson et al. |
| 2022/0330922 A1 | 10/2022 | Sowards et al. |
| 2022/0334251 A1 | 10/2022 | Sowards et al. |
| 2022/0361840 A1* | 11/2022 | Matsumoto ............... G06T 7/70 |
| 2023/0048327 A1 | 2/2023 | Lampe et al. |
| 2023/0107629 A1 | 4/2023 | Sowards et al. |
| 2023/0113291 A1 | 4/2023 | de Wild et al. |
| 2023/0132148 A1 | 4/2023 | Sowards et al. |
| 2023/0135562 A1 | 5/2023 | Misener et al. |
| 2023/0135757 A1 | 5/2023 | Bauer et al. |
| 2023/0148872 A1 | 5/2023 | Sowards et al. |
| 2023/0201539 A1 | 6/2023 | Howell |
| 2023/0277153 A1 | 9/2023 | Sowards et al. |
| 2023/0277154 A1 | 9/2023 | Sowards et al. |
| 2023/0293143 A1 | 9/2023 | Sowards et al. |
| 2023/0338010 A1 | 10/2023 | Sturm |
| 2023/0371928 A1 | 11/2023 | Rajguru et al. |
| 2023/0397900 A1 | 12/2023 | Prince |
| 2024/0065673 A1 | 2/2024 | Sowards et al. |
| 2024/0307024 A1 | 9/2024 | Sowards et al. |
| 2025/0017559 A1 | 1/2025 | Denny et al. |
| 2025/0057501 A1* | 2/2025 | Prince .................. A61B 8/0891 |
| 2025/0104238 A1 | 3/2025 | Misener et al. |

FOREIGN PATENT DOCUMENTS

| | | |
|---|---|---|
| EP | 0933063 A1 | 8/1999 |
| EP | 1504713 A1 | 2/2005 |
| EP | 1591074 B1 | 5/2008 |
| EP | 2823766 A1 | 1/2015 |
| EP | 3181083 A1 | 6/2017 |
| EP | 3870059 | 9/2021 |
| JP | 2000271136 A | 10/2000 |
| JP | 2007222291 A | 9/2007 |
| JP | 2014150928 A | 8/2014 |
| JP | 2018175547 A | 11/2018 |
| KR | 20180070878 A | 6/2018 |
| KR | 102176196 B1 | 11/2020 |
| WO | 2004082749 A2 | 9/2004 |
| WO | 2007115174 A2 | 10/2007 |
| WO | 2010029521 A2 | 3/2010 |
| WO | 2010076808 A1 | 7/2010 |
| WO | 2013059714 A1 | 4/2013 |
| WO | 2014/115150 A1 | 7/2014 |
| WO | 2015/017270 A1 | 2/2015 |
| WO | 2016081023 A1 | 5/2016 |
| WO | 2017096487 A1 | 6/2017 |
| WO | 2017214428 A1 | 12/2017 |
| WO | 2018/026878 A1 | 2/2018 |
| WO | 2018134726 A1 | 7/2018 |
| WO | 2019/232451 A1 | 12/2019 |
| WO | 2020/002620 A1 | 1/2020 |
| WO | 2020/016018 A1 | 1/2020 |
| WO | 2019/232454 A9 | 2/2020 |
| WO | 2020/044769 A1 | 3/2020 |
| WO | 2020067897 A1 | 4/2020 |
| WO | 2020083660 A1 | 4/2020 |
| WO | 2020/186198 A1 | 9/2020 |
| WO | 2021123905 A2 | 6/2021 |
| WO | 2021198226 A1 | 10/2021 |
| WO | 2022/072727 A2 | 4/2022 |
| WO | 2022/081904 A1 | 4/2022 |
| WO | 2022069208 A1 | 4/2022 |
| WO | 2022/119853 A1 | 6/2022 |
| WO | 2022115479 A1 | 6/2022 |
| WO | 2022119856 A1 | 6/2022 |
| WO | 2022221703 A1 | 10/2022 |
| WO | 2022221714 A1 | 10/2022 |
| WO | 2023059512 A1 | 4/2023 |
| WO | 2023076268 A1 | 5/2023 |
| WO | 2023081220 A1 | 5/2023 |
| WO | 2023081223 A1 | 5/2023 |
| WO | 2023091424 A1 | 5/2023 |
| WO | 2023167866 A1 | 9/2023 |

(56) References Cited

FOREIGN PATENT DOCUMENTS

| WO | 2023177718 A1 | 9/2023 |
|---|---|---|
| WO | 2024044277 A1 | 2/2024 |
| WO | 2025/015198 A1 | 1/2025 |

OTHER PUBLICATIONS

U.S. Appl. No. 17/471,015, filed Sep. 9, 2021 Advisory Action dated Feb. 2, 2024.
U.S. Appl. No. 17/534,099, filed Nov. 23, 2021 Advisory Action dated Dec. 8, 2023.
U.S. Appl. No. 17/538,943, filed Nov. 30, 2021 Non-Final Office Action dated Jan. 30, 2024.
U.S. Appl. No. 17/684,180, filed Mar. 1, 2022 Final Office Action dated Jan. 18, 2024.
U.S. Appl. No. 17/722,11, filed Apr. 15, 2022 Non-Final Office Action dated Dec. 22, 2023.
U.S. Appl. No. 17/722,151, filed Apr. 15, 2022 Advisory Action dated Jan. 2, 2024.
U.S. Appl. No. 17/894,460, filed Aug. 24, 2022 Final Office Action dated Jan. 31, 2024.
Lu Zhenyu et al "Recent advances in 5 robot-assisted echography combining perception control and cognition." Cognitive Computation and Systems the Institution of Engineering and Technology, Michael Faraday House, Six Hills Way, Stevenage Herts. SG1 2AY Uk vol. 2 No. 3 Sep. 2, 2020 (Sep. 2, 2020).
Pagoulatos, N. et al. "New spatial localizer based on fiber optics with applications in 3D ultrasound imaging" Proceeding of Spie, vol. 3976 (Apr. 18, 2000; Apr. 18, 2000).
PCT/US2021/049294 filed Sep. 7, 2021 International Search Report and Written Opinion dated Dec. 8, 2021.
PCT/US2021/049712 filed Sep. 9, 2021 International Search Report and Written Opinion dated Dec. 14, 2021.
PCT/US2021/060622 filed Nov. 23, 2021 International Search Report and Written Opinion dated Mar. 3, 2022.
PCT/US2021/061267 filed Nov. 30, 2021 International Search Report and Written Opinion dated Mar. 9, 2022.
PCT/US2021/061276 filed Nov. 30, 2021 International Search Report and Written Opinion dated Mar. 9, 2022.
PCT/US2022/025082 filed Apr. 15, 2022 International Search Report and Written Opinion dated Jul. 11, 2022.
PCT/US2022/025097 filed Apr. 15, 2022 International Search Report and Written Opinion dated Jul. 8, 2022.
Sebastian Vogt: "Real-Time Augmented Reality for Image-Guided Interventions", Oct. 5, 2009, XPO55354720, Retrieved from the Internet: URL: https://opus4.kobv.de/opus4-fau/frontdoor/deliver/index/docld/1235/file/SebastianVogtDissertation.pdf.
U.S. Appl. No. 15/650,474, filed Jul. 14, 2017 Final Office Action dated Jun. 2, 2020.
U.S. Appl. No. 15/650,474, filed Jul. 14, 2017 Non-Final Office Action dated Dec. 16, 2019.
U.S. Appl. No. 15/650,474, filed Jul. 14, 2017 Notice of Allowance dated Dec. 11, 2020.
U.S. Appl. No. 15/650,474, filed Jul. 14, 2017 Notice of Allowance dated Mar. 1, 2021.
U.S. Appl. No. 17/020,476, filed Sep. 14, 2020 Advisory Action dated Aug. 19, 2022.
U.S. Appl. No. 17/020,476, filed Sep. 14, 2020 Final Office Action dated Jun. 9, 2022.
U.S. Appl. No. 17/020,476, filed Sep. 14, 2020 Non-Final Office Action dated Feb. 9, 2022.
U.S. Appl. No. 17/020,476, filed Sep. 14, 2020 Non-Final Office Action dated Sep. 23, 2022.
U.S. Appl. No. 17/471,015, filed Sep. 9, 2021 Non-Final Office Action dated Aug. 16, 2022.
William F Garrett et al: "Real-time incremental visualization of dynamic ultrasound volumes using parallel BSP trees", Visualization '96. Proceedings, IEEE, NE, Oct. 27, 1996, pp. 235-ff, XPO58399771, ISBN: 978-0-89791-864-0 abstract, figures 1-7, pp. 236-240.
PCT/US2023/014143 filed Feb. 28, 2023 International Search Report and Written Opinion dated Jun. 12, 2023.
PCT/US2023/015266 filed Mar. 15, 2023 International Search Report and Written Opinion dated May 25, 2023.
U.S. Appl. No. 17/684,180, filed Mar. 1, 2022 Non-Final Office Action dated Jul. 28, 2023.
PCT/US2022/048716 filed Nov. 2, 2022 International Search Report and Written Opinion dated Feb. 24, 2023.
PCT/US2022/048722 filed Nov. 2, 2022 International Search Report and Written Opinion dated Feb. 24, 2023.
PCT/US2022/049983 filed Nov. 15, 2022 International Search Report and Written Opinion dated Mar. 29, 2023.
PCT/US2022047727 filed Oct. 25, 2022 International Search Report and Written Opinion dated Jan. 25, 2023.
Saxena Ashish et al Thermographic venous blood flow characterization with external cooling stimulation Infrared Physics and Technology Elsevier Science GB vol. 90 Feb. 9, 2018 Feb. 9, 2018 pp. 8-19 XP085378852.
U.S. Appl. No. 17/020,476, filed Sep. 14, 2020 Final Office Action dated Jan. 5, 2023.
U.S. Appl. No. 17/020,476, filed Sep. 14, 2020 Notice of Allowance dated Apr. 28, 2022.
U.S. Appl. No. 17/468,318, filed Sep. 7, 2021 Non-Final Office Action dated Apr. 12, 2023.
U.S. Appl. No. 17/471,015, filed Sep. 9, 2021 Non-Final Office Action dated Mar. 30, 2023.
U.S. Appl. No. 17/534,099, filed Nov. 23, 2021 Non-Final Office Action dated Mar. 31, 2023.
U.S. Appl. No. 17/538,911, filed Nov. 30, 2021 Non-Final Office Action dated Mar. 2, 2023.
U.S. Appl. No. 17/684,180, filed Mar. 1, 2022 Restriction Requirement dated May 19, 2023.
EP 20866520.8 filed Apr. 5, 2022 Extended European Search Report dated Aug. 22, 2023.
PCT/US2022/025097 filed Apr. 15, 2021 International Preliminary Report on Patentability dated Oct. 26, 2023.
PCT/US2023/030970 filed Aug. 23, 2023 International Search Report and Written Opinion dated Oct. 30, 2023.
U.S. Appl. No. 17/468,318, filed Sep. 7, 2021 Advisory Action dated Nov. 6, 2023.
U.S. Appl. No. 17/468,318, filed Sep. 7, 2021 Final Office Action dated Sep. 8, 2023.
U.S. Appl. No. 17/471,015, filed Sep. 9, 2021 Final Office Action dated Oct. 12, 2023.
U.S. Appl. No. 17/534,099, filed Nov. 23, 2021 Final Office Action dated Sep. 29, 2023.
U.S. Appl. No. 17/538,911, filed Nov. 30, 2021 Advisory Action dated Nov. 22, 2023.
U.S. Appl. No. 17/538,911, filed Nov. 30, 2021 Final Office Action dated Sep. 13, 2023.
U.S. Appl. No. 17/722,151, filed Apr. 15, 2022 Final Office Action dated Nov. 6, 2023.
U.S. Appl. No. 17/722,151, filed Apr. 15, 2022 Non-Final Office Action dated Sep. 7, 2023.
U.S. Appl. No. 17/894,460, filed Aug. 24, 2022 Non-Final Office Action dated Nov. 6, 2023.
M. Ikhsan, K. K. Tan, AS. Putra, C. F. Kong, et al., "Automatic identification of blood vessel cross-section for central venous catheter placement using a cascading classifier," 39th Annual International Conference of the IEEE Engineering in Medicine and Biology Society (EMBC). pp. 1489-1492 (Year: 2017).
U.S. Appl. No. 17/471,015, filed Sep. 9, 2021 Non-Final Office Action dated Mar. 28, 2024.
U.S. Appl. No. 17/534,099, filed Nov. 23, 2021 Non-Final Office Action dated Mar. 14, 2024.
U.S. Appl. No. 17/538,911, filed Nov. 30, 2021 Notice of Allowance dated Mar. 14, 2024.
U.S. Appl. No. 17/684,180, filed Mar. 1, 2022 Advisory Action dated Apr. 4, 2024.

(56) References Cited

OTHER PUBLICATIONS

U.S. Appl. No. 17/684,180, filed Mar. 1, 2022 Non-Final Office Action dated May 8, 2024.
U.S. Appl. No. 17/722,111, filed Apr. 15, 2022 Final Office Action dated Jul. 12, 2024.
U.S. Appl. No. 17/722,151, filed Apr. 15, 2022 Non-Final Office Action dated Mar. 25, 2024.
U.S. Appl. No. 17/894,460, filed Aug. 24, 2022 Advisory Action dated Apr. 4, 2024.
U.S. Appl. No. 17/979,564, filed Nov. 2, 2022 Non-Final Office Action dated Jun. 5, 2024.
U.S. Appl. No. 18/238,281, filed Aug. 25, 2023 Non-Final Office Action dated Mar. 22, 2024.
U.S. Appl. No. 18/238,281, filed Aug. 25, 2023 Notice of Allowance dated Jul. 16, 2024.
PCT/US2022/045372 filed Sep. 30, 2022 International Search Report and Written Opinion dated Jan. 14, 2023.
U.S. Appl. No. 17/538,943, filed Nov. 30, 2021 Notice of Allowance dated Aug. 14, 2024.
U.S. Appl. No. 17/684,180, filed Mar. 1, 2022 Advisory Action dated Dec. 27, 2024.
U.S. Appl. No. 17/684,180, filed Mar. 1, 2022 Non-Final Office Action dated Jan. 17, 2025.
U.S. Appl. No. 17/722,111, filed Apr. 15, 2022 Notice of Allowance dated Dec. 18, 2024.
U.S. Appl. No. 17/722,151, filed Apr. 15, 2022 Advisory Action dated Dec. 27, 2024.
U.S. Appl. No. 17/894,460, filed Aug. 24, 2022 Final Office Action dated Dec. 31, 2024.
U.S. Appl. No. 17/957,562, filed Sep. 30, 2022 Advisory Action dated Feb. 12, 2025.
U.S. Appl. No. 17/957,562, filed Sep. 30, 2022 Non-Final Office Action dated Jun. 20, 2024.
U.S. Appl. No. 17/973,171, filed Oct. 25, 2022 Non-Final Office Action dated Dec. 6, 2024.
U.S. Appl. No. 17/979,564, filed Nov. 2, 2022 Advisory Action dated Jan. 17, 2025.
U.S. Appl. No. 17/987,698, filed Nov. 15, 2022 Advisory Action dated Feb. 21, 2025.
U.S. Appl. No. 17/987,698, filed Nov. 15, 2022 Final Office Action dated Dec. 13, 2024.
U.S. Appl. No. 18/121,802, filed Mar. 15, 2023 Non-Final Office Action dated Dec. 16, 2024.
U.S. Appl. No. 18/674,601, filed May 24, 2024 Non-Final Office Action dated Jan. 7, 2025.
PCT/US2024/037647 filed Jul. 11, 2024 International Search Report and Written Opinion dated Oct. 16, 2024.
Thermographic venous blood flow characterization with external cooling stimulation (Year: 2018).
U.S. Appl. No. 17/471,015, filed Sep. 9, 2021 Notice of Allowance dated Oct. 29, 2024.
U.S. Appl. No. 17/534,099, filed Nov. 23, 2021 Notice of Allowance dated Sep. 18, 2024.
U.S. Appl. No. 17/684,180, filed Mar. 1, 2022 Final Office Action dated Sep. 23, 2024.
U.S. Appl. No. 17/722,111, filed Apr. 15, 2022 Advisory Action dated Oct. 23, 2024.
U.S. Appl. No. 17/722,151, filed Apr. 15, 2022 Final Office Action dated Sep. 20, 2024.
U.S. Appl. No. 17/894,460, filed Aug. 24, 2022 Non-Final Office Action dated Sep. 25, 2024.
U.S. Appl. No. 17/957,562, filed Sep. 30, 2022 Final Office Action dated Nov. 27, 2024.
U.S. Appl. No. 17/979,564, filed Nov. 2, 2022 Final Office Action dated Oct. 18, 2024.
U.S. Appl. No. 17/987,698, filed Nov. 15, 2022 Non-Final Office Action dated Sep. 20, 2024.
U.S. Appl. No. 18/113,003, filed Feb. 22, 2023 Non-Final Office Action dated Nov. 27, 2024.
U.S. Appl. No. 17/684,180 filed Mar. 1, 2022 Final Office Action dated May 29, 2025.
U.S. Appl. No. 17/722,151 filed Apr. 15, 2022 Non-Final Office Action dated Mar. 21, 2025.
U.S. Appl. No. 17/894,460 filed Aug. 24, 2022 Advisory Action dated Mar. 13, 2025.
U.S. Appl. No. 17/973,171 filed Oct. 25, 2022 Final Office Action dated Apr. 3, 2025.
U.S. Appl. No. 17/978,698 filed Nov. 15, 2022 Non-Final Office Action dated May 23, 2025.
U.S. Appl. No. 18/113,003 filed Feb. 22, 2023 Final Office Action dated Apr. 29, 2025.
U.S. Appl. No. 18/221,318 filed Jul. 12, 2023 Restriction Requirement dated Mar. 28, 2025.
U.S. Appl. No. 18/674,601 filed May 24, 2024 Notice of Allowance dated Mar. 26, 2025.

* cited by examiner

OPTIMIZED FUNCTIONALITY THROUGH INTEROPERATION OF DOPPLER AND IMAGE BASED VESSEL DIFFERENTIATION

PRIORITY

This application claims the benefit of priority to U.S. Provisional Application No. 63/275,242, filed Nov. 3, 2021, which is incorporated by reference in its entirety into this application.

BACKGROUND

Ultrasound imaging is a widely accepted tool for guiding interventional instruments such as needles to targets such as blood vessels or organs in the human body. In order to successfully guide, for example, a needle to a blood vessel using ultrasound imaging, the needle is monitored in real-time both immediately before and after a percutaneous puncture in order to enable a clinician to determine the distance and the orientation of the needle to the blood vessel and ensure successful access thereto. Although, it may be difficult to identify the blood vessel as a vein or artery as portrayed in an ultrasound image.

Doppler ultrasound is a noninvasive approach to estimating the blood flow through your blood vessels by bouncing high-frequency sound waves (ultrasound) off circulating red blood cells. A doppler ultrasound can estimate how fast blood flows by measuring the rate of change in its pitch (frequency). Doppler ultrasound may also detect a direction of blood flow. For example, doppler ultrasound can differentiate an artery from a vein since the direction of blood flow within an artery is generally in the opposite direction from a blood flow within an adjacent vein.

Disclosed herein are systems and methods for enhancing the identification of blood vessels within ultrasound images via doppler ultrasound.

SUMMARY

Disclosed herein is an ultrasound-imaging system including, in some embodiments, an ultrasound probe coupled with a console. The ultrasound probe includes an array of ultrasonic transducers, where activated ultrasonic transducers of the array of ultrasonic transducers are configured to emit generated ultrasound signals into a patient, receive reflected ultrasound signals from the patient, and convert the reflected ultrasound signals into corresponding electrical signals of the ultrasound signals for processing into ultrasound image data and doppler ultrasound data.

The console includes one or more processors and a non-transitory computer-readable medium having stored thereon logic that, when executed by the one or more processors, causes operations including: (i) obtaining an ultrasound image of a predefined target area of the patient, (ii) detecting one or more blood vessels within the ultrasound image, (iii) obtaining doppler ultrasound data pertaining to blood flow within the one or more blood vessels, (iv) determining a condition of the blood flow based at least partially on doppler ultrasound data, and (v) identifying the one or more blood vessels as a vein or alternatively as an artery based at least partially on the condition of the blood flow within the one or more blood vessels.

In some embodiments, the operations further include determining a direction of the blood flow within the one or more blood vessels based on doppler ultrasound data, where the direction is determined with respect to an image plane of the ultrasound image, and the operations further include identifying the one or more blood vessels as a vein or an artery based at least partially on the direction of the blood flow.

In some embodiments, the operations further include determining a magnitude of the blood flow within the one or more blood vessels based on doppler ultrasound data and further identifying the one or more blood vessels as a vein or an artery based at least partially on the magnitude of the blood flow.

In some embodiments, the operations further include determining a pulsatility of the blood flow within the one or more blood vessels based on doppler ultrasound data, comparing the pulsatility with a pulsatility limit stored in memory, and as a result of the comparison, further at least partially identifying the one or more blood vessels (i) as an artery when the pulsatility exceeds the pulsatility limit or (ii) as a vein when the pulsatility is less than the pulsatility limit.

In some embodiments, the system is configured to obtain an ECG signal, and the operations further include determining the pulsatility of the blood flow in coordination with the ECG signal.

In some embodiments, determining the condition includes determining a pulse timing difference between a blood flow pulse within a first blood vessel and a corresponding blood flow pulse within an second blood vessel based on doppler ultrasound data and the operations further include identifying at least one of the first blood vessel or the second blood vessel as a vein or as an artery based at least partially on the pulse timing difference.

In some embodiments, the operations further include determining a cross-sectional shape of the one or more blood vessels and further identifying the one or more blood vessels as a vein or an artery based at least partially on the cross-sectional shape. In further embodiments, identifying the one or more blood vessels based on the cross-sectional shape includes comparing the shape of the one or more blood vessels with an elliptical shape limit stored in memory and further as a result of the comparison, identifying the one or more blood vessels (i) as an artery when the cross-sectional shape is less than the elliptical shape limit or (ii) as a vein when the cross-sectional shape exceeds the elliptical shape limit.

In some embodiments, the operations further include determining a confidence for the identity of the one or more blood vessels based on one or more of the direction of the blood flow, the magnitude of the blood flow, the pulsatility of the blood flow, the pulse timing difference of the blood flow, or the cross-sectional shape.

In some embodiments, the operations further include defining a doppler ultrasound window extending at least partially across the ultrasound image, where the doppler ultrasound window defines a portion of the ultrasound image for obtaining doppler ultrasound data and the doppler ultrasound window encompasses the one or more blood vessels. Defining the doppler ultrasound window may include automatically defining the doppler ultrasound window upon detecting the one or more blood vessels. Defining the doppler ultrasound window may also include receiving an input via an input device of the system and defining the doppler ultrasound window based on the input, where the input includes a selected portion of the ultrasound image. The input device may include a graphical user interface of the display and/or control buttons of the ultrasound probe.

In some embodiments, the ultrasound probe further includes an array of magnetic sensors configured to convert magnetic signals from a magnetized medical device into corresponding electrical signals of the magnetic signals for processing by the processor into position and/or orientation information of the magnetized medical device with respect to the predefined target area. In further embodiments, the operations further include superimposing an iconographic representation of the medical device atop the ultrasound image and the operations may further include defining the doppler ultrasound window based on the position and/or orientation of the iconographic representation of the medical device atop the ultrasound image. In some embodiments, the operations further include selecting a blood vessel of interest from the one or more blood vessels based on the position and/or orientation of the iconographic representation of the medical device atop the ultrasound image.

In some embodiments, the ultrasound probe further includes an accelerometer, a gyroscope, a magnetometer, or a combination thereof configured to provide tracking data to the console, where the tracking data pertains to the position and/or orientation of the ultrasound probe with respect to a trajectory of the one or more blood vessels. In such embodiments, the operations may further include processing the tracking data in combination with obtaining the doppler ultrasound data to enhance an accuracy of the determining of the direction and/or magnitude of blood flow within the one or more blood vessels.

In some embodiments, the operations further include portraying the ultrasound image on a display of the system and superimposing a notification atop the ultrasound image, where the notification includes the identity of the blood vessel. In some embodiments, the notification further includes the confidence for the identity of the blood vessel.

Also disclosed herein is a method of an ultrasound-imaging system including a non-transitory computer-readable medium ("CRM") having executable logic that causes the ultrasound-imaging system to perform a set of operations for ultrasound imaging when the logic is executed by a processor of a console of the ultrasound-imaging system. The method includes activating ultrasonic transducers of an array of ultrasonic transducers of an ultrasound probe communicatively coupled to the console, where the ultrasonic transducers emit generated ultrasound signals into a patient, receive reflected ultrasound signals from the patient, and convert the reflected ultrasound signals into corresponding electrical signals of the ultrasound signals for processing into ultrasound image data and doppler ultrasound data. The method further includes (i) obtaining an ultrasound image of a predefined target area of the patient, (ii) detecting one or more blood vessels within the ultrasound image, (iii) obtaining doppler ultrasound data pertaining to blood flow within the one or more blood vessels, (iv) determining a condition of the blood flow based at least partially on doppler ultrasound data, and (v) identifying the one or more blood vessels as a vein or alternatively as an artery based at least partially on the condition of the blood flow within the one or more blood vessels.

In some embodiments, the method further includes determining a direction of the blood flow within the one or more blood vessels based on doppler ultrasound data, where the direction is determined with respect to an image plane of the ultrasound image, and the method further includes identifying the one or more blood vessels as a vein or an artery based at least partially on the direction of the blood flow.

In some embodiments, the method further includes determining a magnitude of the blood flow within the one or more blood vessels based on doppler ultrasound data and further identifying the one or more blood vessels as a vein or an artery based at least partially on the magnitude of the blood flow.

In some embodiments, the method further includes determining a pulsatility of the blood flow within the one or more blood vessels based on doppler ultrasound data, comparing the pulsatility with a pulsatility limit stored in memory, and as a result of the comparison, further at least partially identifying the one or more blood vessels (i) as an artery when the pulsatility exceeds the pulsatility limit or (ii) as a vein when the pulsatility is less than the pulsatility limit. In some embodiments of the method, the system is configured to obtain an ECG signal, and the method further includes determining the pulsatility of the blood flow in coordination with the ECG signal.

In some embodiments, determining the condition includes determining a pulse timing difference between a blood flow pulse within a first blood vessel and a corresponding blood flow pulse within an second blood vessel based on doppler ultrasound data and the method further includes identifying at least one of the first blood vessel or the second blood vessel as a vein or as an artery based at least partially on the pulse timing difference.

In some embodiments, the method further includes determining a cross-sectional shape of the one or more blood vessels and further identifying the one or more blood vessels as a vein or an artery based at least partially on the cross-sectional shape.

In some embodiments, the method further includes determining a confidence for the identity of the one or more blood vessels based on one or more of the direction of the blood flow, the magnitude of the blood flow, the pulsatility of the blood flow, the pulse timing difference of the blood flow, or the cross-sectional shape.

In some embodiments, the method further includes defining a doppler ultrasound window extending at least partially across the ultrasound image, where the doppler ultrasound window defines a portion of the ultrasound image for obtaining doppler ultrasound data and the doppler ultrasound window encompasses the one or more blood vessels.

In some embodiments of the method, defining the doppler ultrasound window includes automatically defining the doppler ultrasound window upon detecting the one or more blood vessels. In some embodiments of the method defining the doppler ultrasound window includes receiving an input via an input device of the system and defining the doppler ultrasound window based on the input, where the input includes a selected portion of the ultrasound image and where the input device includes one or more of a graphical user interface of the display or control buttons of the ultrasound probe.

In some embodiments, the method further includes portraying the ultrasound image on a display of the system and superimposing a notification atop the ultrasound image, where the notification includes the identity of the blood vessel and/or the confidence for the identity of the blood vessel.

In some embodiments of the method, the ultrasound probe further includes an array of magnetic sensors configured to convert magnetic signals from a magnetized medical device into corresponding electrical signals of the magnetic signals for processing by the processor into position and/or orientation information of the magnetized medical device with respect to the predefined target area. In such embodiments, the method further includes superimposing an iconographic representation of the medical device atop the ultrasound image and defining the doppler ultrasound window based on the position and/or orientation of the iconographic representation of the medical device atop the ultrasound image.

These and other features of the concepts provided herein will become more apparent to those of skill in the art in view of the accompanying drawings and following description, which describe particular embodiments of such concepts in greater detail.

DRAWINGS

DESCRIPTION

Figure 1:
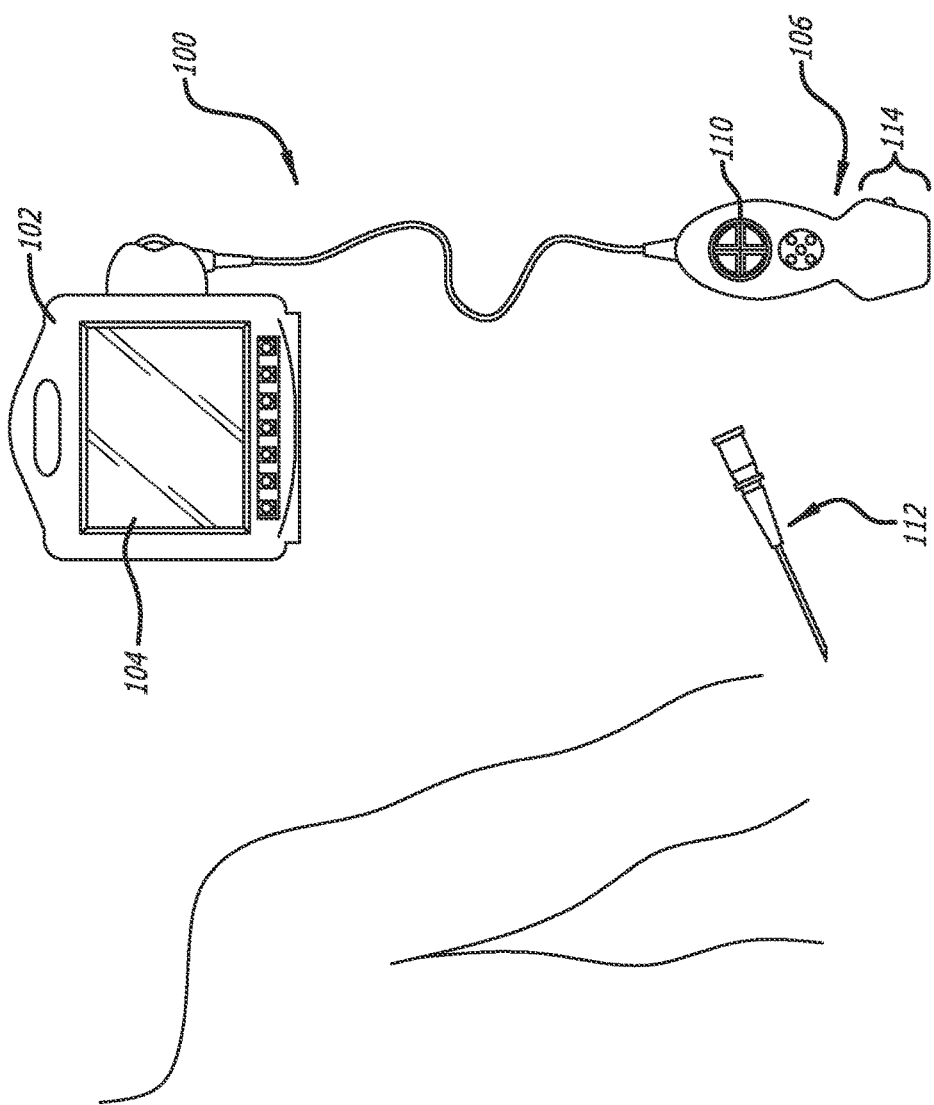
FIG. 1 illustrates an ultrasound-imaging system and a patient in accordance with some embodiments.
Figure 1:
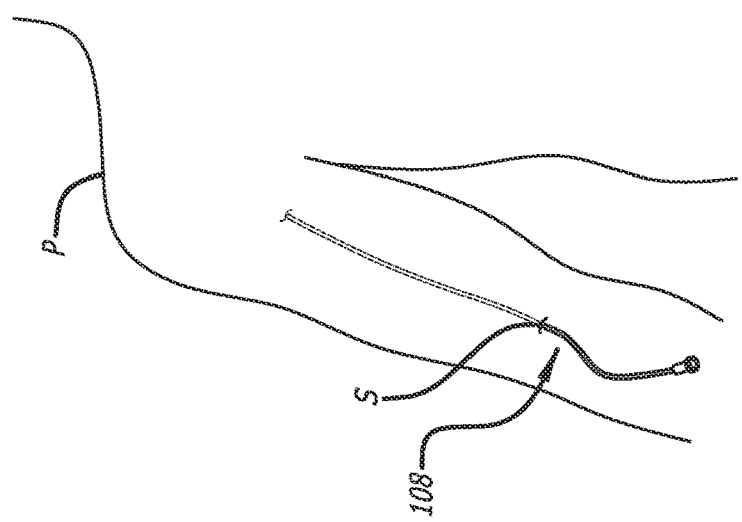

Before some particular embodiments are disclosed in greater detail, it should be understood that the particular embodiments disclosed herein do not limit the scope of the concepts provided herein. It should also be understood that a particular embodiment disclosed herein can have features that can be readily separated from the particular embodiment and optionally combined with or substituted for features of any of a number of other embodiments disclosed herein.

Regarding terms used herein, it should also be understood the terms are for the purpose of describing some particular embodiments, and the terms do not limit the scope of the concepts provided herein. Ordinal numbers (e.g., first, second, third, etc.) are generally used to distinguish or identify different features or steps in a group of features or steps, and do not supply a serial or numerical limitation. For example, "first," "second," and "third" features or steps need not necessarily appear in that order, and the particular embodiments including such features or steps need not necessarily be limited to the three features or steps. Labels such as "left," "right," "top," "bottom," "front," "back," and the like are used for convenience and are not intended to imply, for example, any particular fixed location, orientation, or direction. Instead, such labels are used to reflect, for example, relative location, orientation, or directions. Singular forms of "a," "an," and "the" include plural references unless the context clearly dictates otherwise.

With respect to "proximal," a "proximal portion" or a "proximal-end portion" of, for example, a catheter disclosed herein includes a portion of the catheter intended to be near a clinician when the catheter is used on a patient. Likewise, a "proximal length" of, for example, the catheter includes a length of the catheter intended to be near the clinician when the catheter is used on the patient. A "proximal end" of, for example, the catheter includes an end of the catheter intended to be near the clinician when the catheter is used on the patient. The proximal portion, the proximal-end portion, or the proximal length of the catheter can include the proximal end of the catheter; however, the proximal portion, the proximal-end portion, or the proximal length of the catheter need not include the proximal end of the catheter. That is, unless context suggests otherwise, the proximal portion, the proximal-end portion, or the proximal length of the catheter is not a terminal portion or terminal length of the catheter.

With respect to "distal," a "distal portion" or a "distal-end portion" of, for example, a catheter disclosed herein includes a portion of the catheter intended to be near or in a patient when the catheter is used on the patient. Likewise, a "distal length" of, for example, the catheter includes a length of the catheter intended to be near or in the patient when the catheter is used on the patient. A "distal end" of, for example, the catheter includes an end of the catheter intended to be near or in the patient when the catheter is used on the patient. The distal portion, the distal-end portion, or the distal length of the catheter can include the distal end of the catheter; however, the distal portion, the distal-end portion, or the distal length of the catheter need not include the distal end of the catheter. That is, unless context suggests otherwise, the distal portion, the distal-end portion, or the distal length of the catheter is not a terminal portion or terminal length of the catheter.

Unless defined otherwise, all technical and scientific terms used herein have the same meaning as commonly understood by those of ordinary skill in the art.

Ultrasound-Imaging Systems

Figure 2:
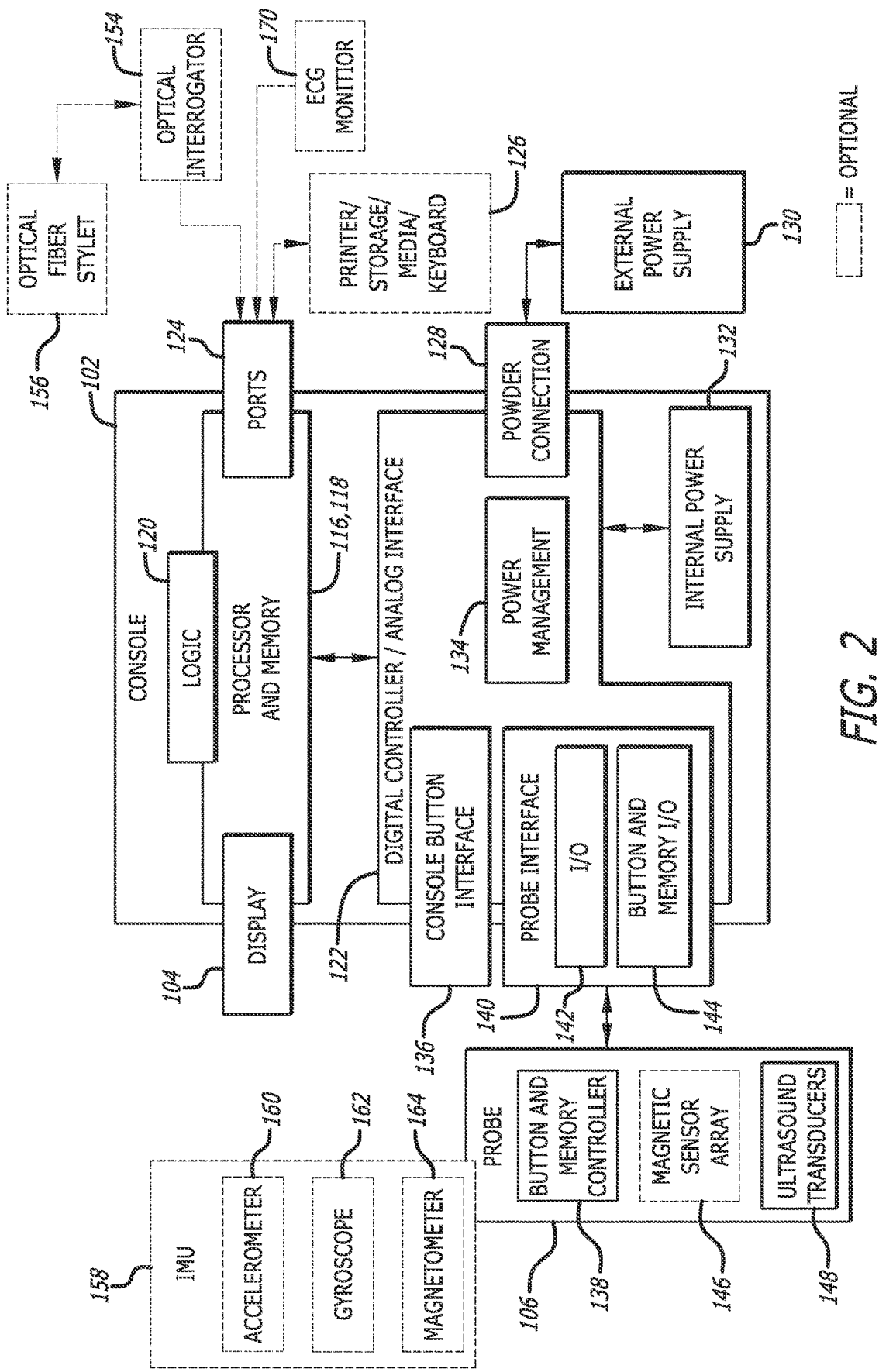
FIG. 2 illustrates a block diagram of a console of the ultrasound-imaging system of FIG. 1 in accordance with some embodiments.
Figure 3B:
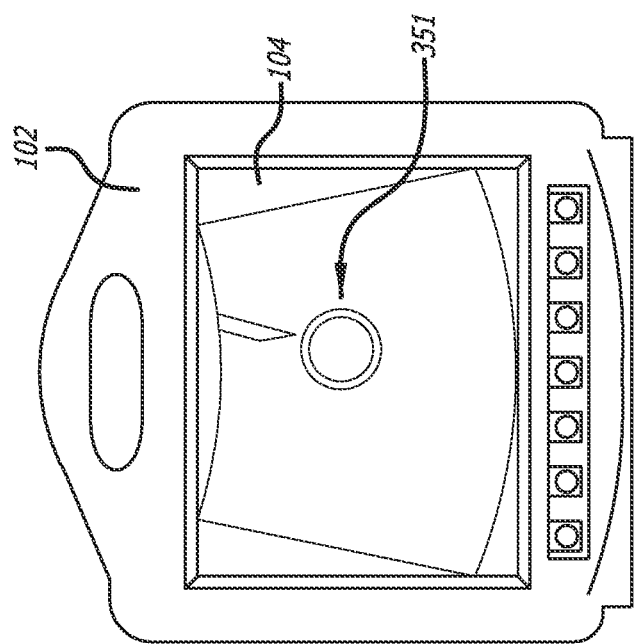
FIG. 3B illustrates an ultrasound image of the blood vessel of FIG. 3A on a display screen of the ultrasound-imaging system in accordance with some embodiments.
Figure 3A:
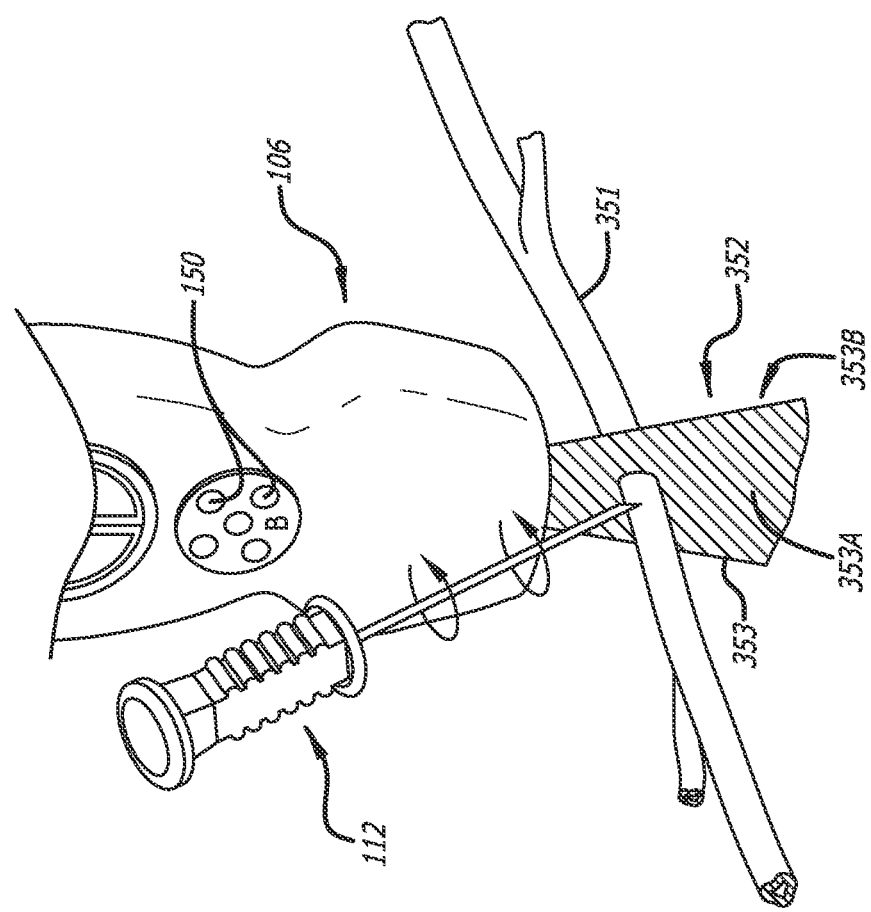
FIG. 3A illustrates an ultrasound probe of the ultrasound-imaging system imaging a blood vessel in accordance with some embodiments.

FIG. 1 illustrates an ultrasound-imaging system 100, a needle 112, and a patient P in accordance with some embodiments. FIG. 2 illustrates a block diagram of the ultrasound-imaging system 100 in accordance with some embodiments. FIG. 3A illustrates an ultrasound probe 106 of the ultrasound-imaging system 100 imaging a blood vessel of the patient P prior to accessing the blood vessel in accordance with some embodiments. FIG. 3B illustrates an ultrasound image of the blood vessel of FIG. 3A on a display screen 104 of the ultrasound-imaging system 100 with an iconographic representation of the needle 112 in accordance with some embodiments.

As shown, the ultrasound-imaging system 100 includes a console 102, the display screen 104, and the ultrasound probe 106. The ultrasound-imaging system 100 is useful for imaging a target such as a blood vessel or an organ within a body of the patient P prior to a percutaneous puncture with the needle 112 for inserting the needle 112 or another medical device into the target and accessing the target. Indeed, the ultrasound-imaging system 100 is shown in FIG. 1 in a general relationship to the patient P during an ultrasound-based medical procedure to place a catheter 108 into the vasculature of the patient P through a skin insertion site S created by a percutaneous puncture with the needle 112. It should be appreciated that the ultrasound-imaging system 100 can be useful in a variety of ultrasound-based medical procedures other than catheterization. For example, the percutaneous puncture with the needle 112 can be performed to biopsy tissue of an organ of the patient P.

The console 102 houses a variety of components of the ultrasound-imaging system 100, and it is appreciated the console 102 can take any of a variety of forms. A processor 116 and memory 118 such as random-access memory ("RAM") or non-volatile memory (e.g., electrically erasable programmable read-only memory ["EEPROM"]) is included in the console 102 for controlling functions of the ultrasound-imaging system 100, as well as executing various logic operations or algorithms during operation of the ultrasound-imaging system 100 in accordance with executable logic 120 therefor stored in the memory 118 for execution by the processor 116. For example, the console 102 is configured to instantiate by way of the logic 120 one or more processes for adjusting a distance of activated ultrasonic transducers 149 from a predefined target area (e.g., an area including a blood vessel), an orientation of the activated ultrasonic transducers 149 to the predefined target area, or both the distance and the orientation of the activated ultrasonic transducers 149 with respect to the predefined target area, as well as process electrical signals from the ultrasound probe 106 into ultrasound images. Adjusting the activated ultrasonic transducers 149 uses ultrasound-imaging data, magnetic-field data, shape-sensing data, or a combination thereof received by the console 102 for activating certain ultrasonic transducers of a 2-D array of the ultrasonic transducers 148 or moving those already activated in a linear array of the ultrasonic transducers 148. A digital controller/analog interface 122 is also included with the console 102 and is in communication with both the processor 116 and other system components to govern interfacing between the ultrasound probe 106 and other system components set forth herein.

The ultrasound-imaging system 100 further includes ports 124 for connection with additional components such as optional components 126 including a printer, storage media, keyboard, etc. The ports 124 can be universal serial bus ("USB") ports, though other types of ports can be used for this connection or any other connections shown or described herein. A power connection 128 is included with the console 102 to enable operable connection to an external power supply 130. An internal power supply 132 (e.g., a battery) can also be employed either with or exclusive of the external power supply 130. Power management circuitry 134 is included with the digital controller/analog interface 122 of the console 102 to regulate power use and distribution.

Optionally, a stand-alone optical interrogator 154 can be communicatively coupled to the console 102 by way of one of the ports 124. Alternatively, the console 102 can include an integrated optical interrogator integrated into the console 102. Such an optical interrogator is configured to emit input optical signals into a companion optical-fiber stylet 156 for shape sensing with the ultrasound-imaging system 100, which optical-fiber stylet 156, in turn, is configured to be inserted into a lumen of a medical device such as the needle 112, and convey the input optical signals from the optical interrogator 154 to a number of FBG sensors along a length of the optical-fiber stylet 156. The optical interrogator 154 is also configured to receive reflected optical signals conveyed by the optical-fiber stylet 156 reflected from the number of FBG sensors, the reflected optical signals indicative of a shape of the optical-fiber stylet 156. The optical interrogator 154 is also configured to convert the reflected optical signals into corresponding electrical signals for processing by the console 102 into distance and orientation information with respect to the target for adjusting a distance of the activated ultrasonic transducers 149, an orientation of the activated ultrasonic transducers 149, or both the distance and the orientation of the activated ultrasonic transducers 149 with respect to the target or the medical device when it is brought into proximity of the target. For example, the distance and orientation of the activated ultrasonic transducers 149 can be adjusted with respect to a blood vessel as the target. Indeed, an image plane can be established by the activated ultrasonic transducers 149 being perpendicular or parallel to the blood vessel in accordance with an orientation of the blood vessel. The distance and orientation information can also be used for displaying an iconographic representation of the medical device on the display.

The system 100 may optionally include an ECG monitor 170 communicatively coupled with the console 102 by way of one of the ports 124. Alternatively, the console 102 can include an ECG monitor integrated into the console 102. The ECG monitor 170 includes one or more electrodes (not shown) coupleable with the patient P for obtaining ECG signals. The ECG monitor 170 is configured to receive the ECG signals from the electrodes coupled with the patient P and convert the ECG signals into electrical signals for processing by the console 102.

The display screen 104 is integrated into the console 102 to provide a GUI and display information for a clinician during such as one-or-more ultrasound images of the target area of the patient P attained by the ultrasound probe 106. In addition, the ultrasound-imaging system 100 enables the distance and orientation of a magnetized medical device such as the needle 112 to be superimposed in real-time atop an ultrasound image of the target, thus enabling a clinician to accurately guide the magnetized medical device to an intended target. Notwithstanding the foregoing, the display screen 104 can alternatively be separate from the console 102 and communicatively coupled thereto. A console button interface 136 and control buttons 110 (see FIG. 1) included on the ultrasound probe 106 can be used to immediately call up a desired mode to the display screen 104 by the clinician for assistance in an ultrasound-based medical procedure. In some embodiments, the display screen 104 is an LCD device.

The ultrasound probe 106 is employed in connection with ultrasound-based visualization of a target such as a blood vessel (see FIG. 3A) in preparation for inserting the needle 112 or another medical device into the target. Such visualization gives real-time ultrasound guidance and assists in reducing complications typically associated with such insertion, including inadvertent arterial puncture, hematoma, pneumothorax, etc. As described in more detail below, the ultrasound probe 106 is configured to provide to the console 102 electrical signals corresponding to both the ultrasound-imaging data, the magnetic-field data, the shape-sensing data, or a combination thereof for the real-time ultrasound guidance.

Figure 4:
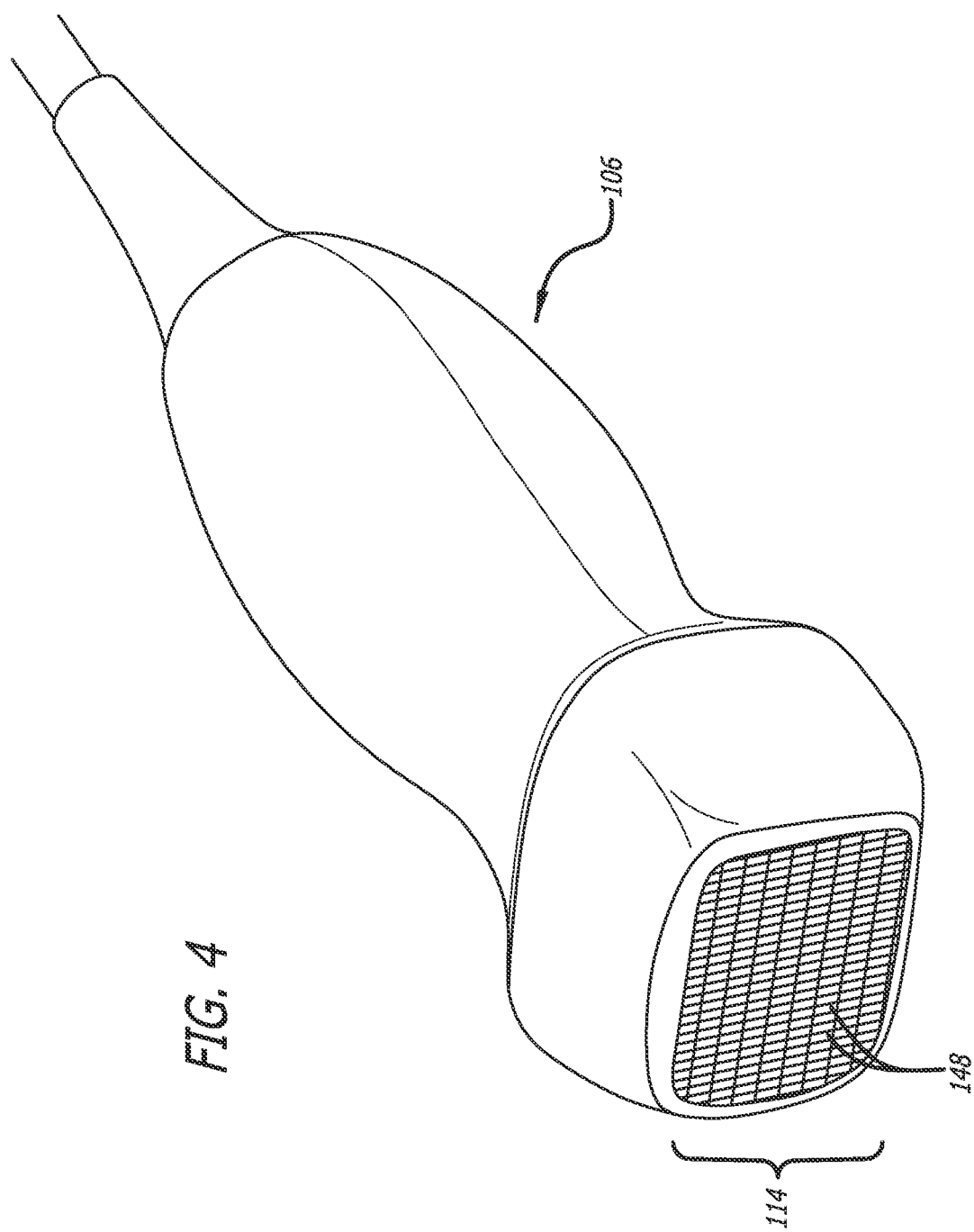
FIG. 4 illustrates the ultrasound probe of the ultrasound-imaging system configured as a 2-D ultrasound probe in accordance with some embodiments.

FIG. 4 illustrates the ultrasound probe 106 of the ultrasound-imaging system 100 configured as a 2-D ultrasound probe 106 in accordance with some embodiments. The ultrasound probe 106 includes a probe head 114 that houses a mounted and moveable (e.g., translatable or rotatable along a central axis) linear array of the ultrasonic transducers 148 or a 2-D array of the ultrasonic transducers 148, wherein the ultrasonic transducers 148 are piezoelectric transducers or capacitive micro-machined ultrasonic transducers ("CMUTs"). When the ultrasound probe 106 is configured with the 2-D array of the ultrasonic transducers 148, a subset of the ultrasonic transducers 148 is linearly activated as needed for ultrasound imaging in accordance with ultrasound-imaging data, magnetic-field data, shape-sensing data, or a combination thereof to maintain the target in an image plane or switch to a different image plane (e.g., from perpendicular to a medical-device plane to parallel to the medical-device plane) including the target.

The probe head 114 is configured for placement against skin of the patient P proximate a prospective needle-insertion site where the activated ultrasonic transducers 149 in the probe head 114 can generate and emit the generated ultrasound signals into the patient P in a number of pulses, receive reflected ultrasound signals or ultrasound echoes from the patient P by way of reflection of the generated ultrasonic pulses by the body of the patient P, and convert the reflected ultrasound signals into corresponding electrical signals for processing into ultrasound images by the console 102 to which the ultrasound probe 106 is communicatively coupled. In this way, a clinician can employ the ultrasound-imaging system 100 to determine a suitable insertion site and establish vascular access with the needle 112 or another medical device.

The ultrasound probe 106 further includes the control buttons 110 for controlling certain aspects of the ultrasound-imaging system 100 during an ultrasound-based medical procedure, thus eliminating the need for the clinician to reach out of a sterile field around the patient P to control the ultrasound-imaging system 100. For example, a control button of the control buttons 110 can be configured to select or lock onto the target (e.g., a blood vessel, an organ, etc.) when pressed for visualization of the target in preparation for inserting the needle 112 or another medical device into the target. Such a control button can also be configured to deselect the target, which is useful whether the target was selected by the control button or another means such as by holding the ultrasound probe 106 stationary over the target to select the target, issuing a voice command to select the target, or the like.

FIG. 2 shows that the ultrasound probe 106 further includes a button and memory controller 138 for governing button and ultrasound probe 106 operation. The button and memory controller 138 can include non-volatile memory (e.g., EEPROM). The button and memory controller 138 is in operable communication with a probe interface 140 of the console 102, which includes an input/output ("I/O") component 142 for interfacing with the ultrasonic transducers 148 and a button and memory I/O component 144 for interfacing with the button and memory controller 138.

Also as seen in FIGS. 2 and 3A, the ultrasound probe 106 can include a magnetic-sensor array 146 for detecting a magnetized medical device such as the needle 112 during ultrasound-based medical procedures. The magnetic-sensor array 146 includes a number of magnetic sensors 150 embedded within or included on a housing of the ultrasound probe 106. The magnetic sensors 150 are configured to detect a magnetic field or a disturbance in a magnetic field as magnetic signals associated with the magnetized medical device when it is in proximity to the magnetic-sensor array 146. The magnetic sensors 150 are also configured to convert the magnetic signals from the magnetized medical device (e.g., the needle 112) into electrical signals for the console 102 to process into distance and orientation information for the magnetized medical device with respect to the predefined target, as well as for display of an iconographic representation of the magnetized medical device on the display screen 104. (See the magnetic field B of the needle 112 in FIG. 3A.) Thus, the magnetic-sensor array 146 enables the ultrasound-imaging system 100 to track the needle 112 or the like.

Though configured here as magnetic sensors, it is appreciated that the magnetic sensors 150 can be sensors of other types and configurations. Also, though they are described herein as included with the ultrasound probe 106, the magnetic sensors 150 of the magnetic-sensor array 146 can be included in a component separate from the ultrasound probe 106 such as a sleeve into which the ultrasound probe 106 is inserted or even a separate handheld device. The magnetic sensors 150 can be disposed in an annular configuration about the probe head 114 of the ultrasound probe 106, though it is appreciated that the magnetic sensors 150 can be arranged in other configurations, such as in an arched, planar, or semi-circular arrangement.

Each magnetic sensor of the magnetic sensors 150 includes three orthogonal sensor coils for enabling detection of a magnetic field in three spatial dimensions. Such 3-dimensional ("3-D") magnetic sensors can be purchased, for example, from Honeywell Sensing and Control of Morristown, NJ. Further, the magnetic sensors 150 are configured as Hall-effect sensors, though other types of magnetic sensors could be employed. Further, instead of 3-D sensors, a plurality of 1-dimensional ("1-D") magnetic sensors can be included and arranged as desired to achieve 1-, 2-, or 3-D detection capability.

Five magnetic sensors 150 are included in the magnetic-sensor array 146 so as to enable detection of a magnetized medical device such as the needle 112 in three spatial dimensions (e.g., X, Y, Z coordinate space), as well as the pitch and yaw orientation of the magnetized medical device itself. Detection of the magnetized medical device in accordance with the foregoing when the magnetized medical device is brought into proximity of the ultrasound probe 106 allows for dynamically adjusting a distance of the activated ultrasonic transducers 149, an orientation of the activated ultrasonic transducers 149, or both the distance and the orientation of the activated ultrasonic transducers 149 with respect to the target or the magnetized medical device. For example, the distance and orientation of the activated ultrasonic transducers 149 can be adjusted with respect to a blood vessel as the target. Indeed, an image plane can be established by the activated ultrasonic transducers 149 being perpendicular or parallel to the blood vessel in accordance with an orientation of the blood vessel. Note that in some embodiments, orthogonal sensing components of two or more of the magnetic sensors 150 enable the pitch and yaw attitude of the magnetized medical device to be determined, which enables tracking with relatively high accuracy. In other embodiments, fewer than five or more than five magnetic sensors of the magnetic sensors 150 can be employed in the magnetic-sensor array 146. More generally, it is appreciated that the number, size, type, and placement of the magnetic sensors 150 of the magnetic-sensor array 146 can vary from what is explicitly shown here.

As shown in FIG. 2, the ultrasound probe 106 can further include an inertial measurement unit ("IMU") 158 or any one or more components thereof for inertial measurement selected from an accelerometer 160, a gyroscope 162, and a magnetometer 164 configured to provide positional-tracking data of the ultrasound probe 106 to the console 102 for tracking the position and/or orientation of the image plane.

The processor 116 is further configured to execute the logic 120 for processing the positional-tracking data for assessing a distance of the activated ultrasonic transducers 149 from the blood vessel, the orientation of the activated ultrasonic transducers 149 with respect to the blood vessel, or both the distance and the orientation of the activated ultrasonic transducers 149 with respect to the blood vessel to define an orientation of the image plane with respect the blood vessel.

It is appreciated that a medical device of a magnetizable material enables the medical device (e.g., the needle 112) to be magnetized by a magnetizer, if not already magnetized, and tracked by the ultrasound-imaging system 100 when the magnetized medical device is brought into proximity of the magnetic sensors 150 of the magnetic-sensor array 146 or inserted into the body of the patient P during an ultrasound-based medical procedure. Such magnetic-based tracking of the magnetized medical device assists the clinician in placing a distal tip thereof in a desired location, such as in a lumen of a blood vessel, by superimposing a simulated needle image representing the real-time distance and orientation of the needle 112 over an ultrasound image of the body of the patient P being accessed by the magnetized medical device. Such a medical device can be stainless steel such as SS 304 stainless steel; however, other suitable needle materials that are capable of being magnetized can be employed. So configured, the needle 112 or the like can produce a magnetic field or create a magnetic disturbance in a magnetic field detectable as magnetic signals by the magnetic-sensor array 146 of the ultrasound probe 106 so as to enable the distance and orientation of the magnetized medical device to be tracked by the ultrasound-imaging system 100 for adjusting the distance of the activated ultrasonic transducers 149, an orientation of the activated ultrasonic transducers 149, or both the distance and the orientation of the activated ultrasonic transducers 149 with respect to the magnetized medical device.

During operation of the ultrasound-imaging system 100, the probe head 114 of the ultrasound probe 106 is placed against skin of the patient P. An ultrasound beam 352 is produced so as to ultrasonically image a portion of a target area that may include a blood vessel beneath a surface of the skin of the patient P such as the blood vessel 351 of FIG. 3A. (See FIG. 3A.). The ultrasound beam defines an image plane 353 having a front side 353A consistent with a front side of the ultrasound probe 106 and an opposite facing back side 353B. The ultrasonic image of the blood vessel 351 can be depicted and stabilized on the display screen 104 of the ultrasound-imaging system 100 as shown in FIG. 3B.

Figure 5B:
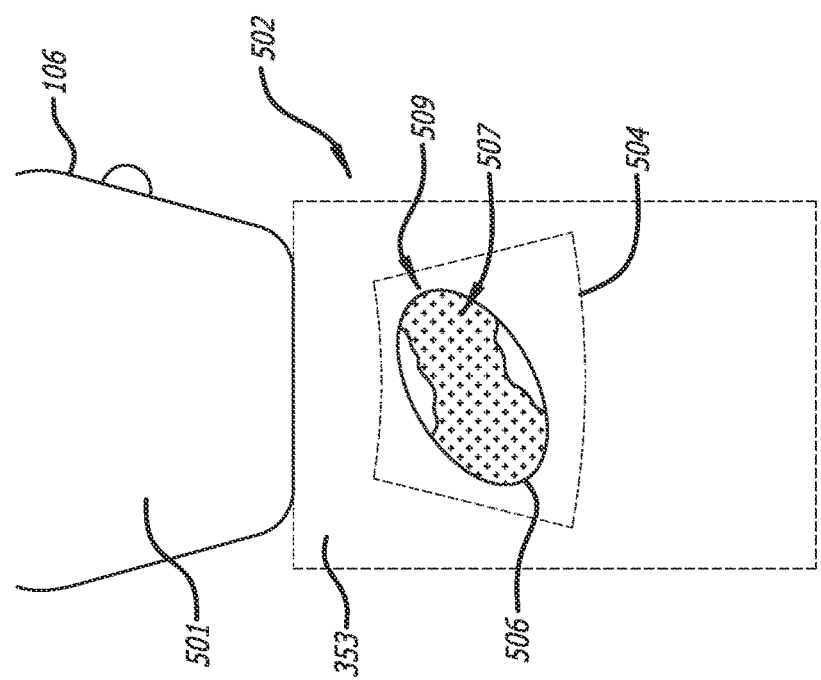
FIG. 5B illustrate the exemplary subcutaneous target area of FIG. 5A further illustrating the application of doppler ultrasound in accordance with some embodiments.
Figure 5A:
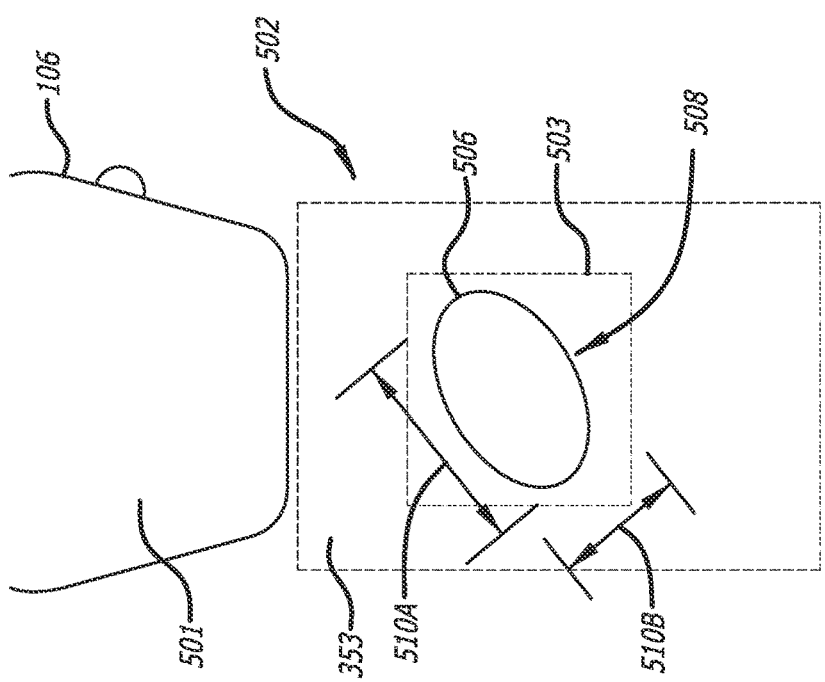
FIG. 5A illustrate an exemplary subcutaneous target area of a patient including a blood vessel for ultrasound imaging in accordance with some embodiments.

FIGS. 5A-5B illustrate a subcutaneous target area of a patient for ultrasound imaging (i.e., for display in an ultrasound image) in accordance with some embodiments. Referring to FIG. 5A, the predefined target area 502 for defining the ultrasound image includes a blood vessel 506 shown in conjunction with an image plane 353 (see FIG. 3A) defined by the ultrasound probe 106. For illustration purposes, the predefined target area 502 may be synonymous with an ultrasound image that may be portrayed on the display 104.

In some embodiments, the system 100 may determine or otherwise define a region 503 of the predefined target area 502 that encompasses the blood vessel 506. In some instances, the identity of the blood vessel 506 as a vein vs. an artery may be unknown. According to some embodiments, the system 100 is configured to determine the identity of the blood vessel 506 as a vein or alternatively as an artery. In other embodiments, the system 100 may also be configured to determine the identity of one or more other anatomical elements within the ultrasound image, such as one or more nerves, for example. In some instances, the blood vessel 506 may be one of a plurality of the blood vessels (not shown) located within the predefined target area 502. As such, the system 100 may be configured to determine the identity of more than one blood vessel within the ultrasound image.

The image plane 353 as defined by the ultrasound probe 106 may be oriented to be perpendicular to the blood vessel 506. In other words, the clinician may adjust the position and/or orientation of the ultrasound probe 106 to establish an orientation of the image plane that is perpendicular to the blood vessel 506.

In some embodiments, the identity of the blood vessel 506 may be at least partially determined by a proximity of the blood vessel 506 with respect to the ultrasound probe 106. In other words, for some patients, the identity of the blood vessel 506 may be readily apparent due to a clinician awareness of the target area. For example, in some instances, the clinician may easily identify a basilic vein within a patient's arm. However, in other instances, the identification of the blood vessel 506 may be difficult to assess based on anatomical structure.

Typically, a blood pressure within an artery is greater than a blood pressure within a vein. Similarly, the structure of an artery may include a thicker wall than a vein. As such, a cross-sectional shape of an artery may often be rounder than a cross-section shape of a vein. More specifically, the cross-sectional shape of a vein may be more elliptical, or otherwise elongated, in contrast to the cross-sectional shape of an artery. In some embodiments, a length 510A and a width 510B of the blood vessel 506 may be obtained from ultrasound image data and processed according to the logic 120 to assess the shape of the blood vessel 506. Accordingly, the identity of the blood vessel 506 may be determined based on the cross-sectional shape as further describe below.

With reference to FIG. 5B, the identity of the blood vessel 506 may be determined based on a direction of blood flow within the blood vessel 506. As the direction of the blood flow is in opposite directions in veins vs. arteries, an assessment of the blood flow direction may assist in identifying the blood vessel 506. As the ultrasound probe 106 is configured to perform doppler ultrasound, the ultrasound probe 106 may obtain doppler ultrasound data. Therefrom, the logic 120 may determine a direction of the blood flow within the blood vessel 506 with respect to the image plane 353 (i.e., an orientation of the ultrasound probe 106). In other words, in an instance where the clinician has oriented ultrasound probe 106 on the patient's arm so that a front side 501 of the ultrasound probe faces the patient's hand, a blood flow direction 507 (illustrated as going into the page) within the blood vessel 506 extending from the front side 501 of the ultrasound probe 106 toward the back side of the ultrasound probe 106 may be consistent with blood flow through a vein. Alternatively, a blood flow direction 507 within the blood vessel 506 extending from the back side of the ultrasound probe 106 toward the front side 501 (i.e., an opposite direction from the blood flow direction 507) may be consistent with blood flow through an artery. As such, the logic 120, upon determining direction of blood flow within blood vessel 506, may identify the blood vessel 506 as a vein or alternatively an artery based on doppler ultrasound data.

In some instances, the anatomy of the patient and/or a vasculature operation of the patient may introduce some error in the determination of the blood flow direction within the blood vessel 506. Such an instance may include a partially occluded or totally occluded blood vessel 506. In some embodiments, the logic 120 may determine a confidence for the identification of the blood vessel 506 based on the direction of blood flow as further described below.

In some embodiments, the identification of the blood vessel may be determined via a magnitude (e.g., a velocity or flow rate) of blood flow within the blood vessel 506. In some instances, a medical procedure may include identifying one blood vessel in relation to an adjacent blood vessel. For example, in some instances, a blood flow rate through an artery may generally be greater than a blood flow through an adjacent vein. As such, the identification of the blood vessel 506 may be determined in accordance with a magnitude of blood flow with the blood vessel 506 as further described below. In some embodiments, the logic 120 may also determine a confidence for the identification of the blood vessel 506 based on the magnitude of blood flow as further described below.

In some embodiments, the cross-section shape of the blood vessel 506, such as the cross-section shape 508 of FIG. 5A may be determined via ultrasound image data. In further embodiments, a blood flow related cross-section shape 509 of the blood vessel 506 may be determined via doppler ultrasound data as shown in the FIG. 5B. In some instances, the cross-section shape 509 may be more elongated than the cross-section shape 508, which may enhance (e.g., increase the accuracy of) the determination of the identity of the blood vessel 506 based on the cross-section shape. In some embodiments, the logic 120 may also determine a confidence for the identification of the blood vessel 506 based on the shape of the blood vessel.

In some embodiments, the identification of the blood vessel 506 may include an assessment of a pulsatility of the blood flow. Typically, arterial blood flow is more pulsatile in accordance with the heartbeat than venous blood flow. As such, the pulsatility of the blood flow within the blood vessel 506 may be used to identify the blood vessel 506. According to one embodiment, the ultrasound probe 106 may obtain pulsatility data (i.e., doppler ultrasound data pertaining to the pulsatility of the blood flow) and provide the pulsatility data to the console 102 for processing. The logic 120 may then determine the identity of the blood vessel 506 based on the pulsatility data as further described below. In some embodiments, the logic 120 may also determine a confidence for the identification of the blood vessel 506 based on the pulsatility of the blood flow.

In some instances, the blood flow within the blood vessel 506 may be uneven (i.e., pulsatile) due to factors other than the heartbeat. In such instances, it may be advantageous to isolate the pulsatility related to the heartbeat from uneven flow caused by other factors. So doing may enhance an accuracy of a pulsatility assessment/measurement. As stated above, the system 100 may include an ECG monitor 170 for providing an ECG signal to the console 102. The logic 120 may in some embodiments, utilize the ECG signal to isolate the pulsatility of the heartbeat from the uneven flow caused by other factors as further described below. In other words, the assessment of the pulsatility of the blood flow may be performed in coordination with the ECG signal.

The doppler ultrasound data may be obtained within a defined doppler ultrasound window 504 defining a portion of the ultrasound image. In other words, the logic 120 may define a portion of the ultrasound image within which motion/movement of elements may be assessed via doppler ultrasound. The doppler ultrasound window 504 encompasses at least the blood vessel 506 but may also encompass more than one blood vessel and/or other anatomical elements, such as nerves, for example.

In some embodiments, the doppler ultrasound window 504 may be automatically defined in accordance with detecting the blood vessel 506 within the predefined target area 502, i.e., the doppler ultrasound window 504 may be automatically defined upon detecting the one or more blood vessels.

In some embodiments, the clinician may define the doppler ultrasound window 504 via input to the system 100 through an input device such as a computer mouse or other pointing device. In some embodiments, the input may be facilitated via a GUI interface of the display 104. In other embodiments, the input may be facilitated via the control buttons 110 (see FIG. 1) on the ultrasound probe 106. In some embodiments, the clinician may select the blood vessel 506 as a target blood vessel (or a blood vessel on interest) from among other blood vessel that may be included in the ultrasound image.

Figure 6B:
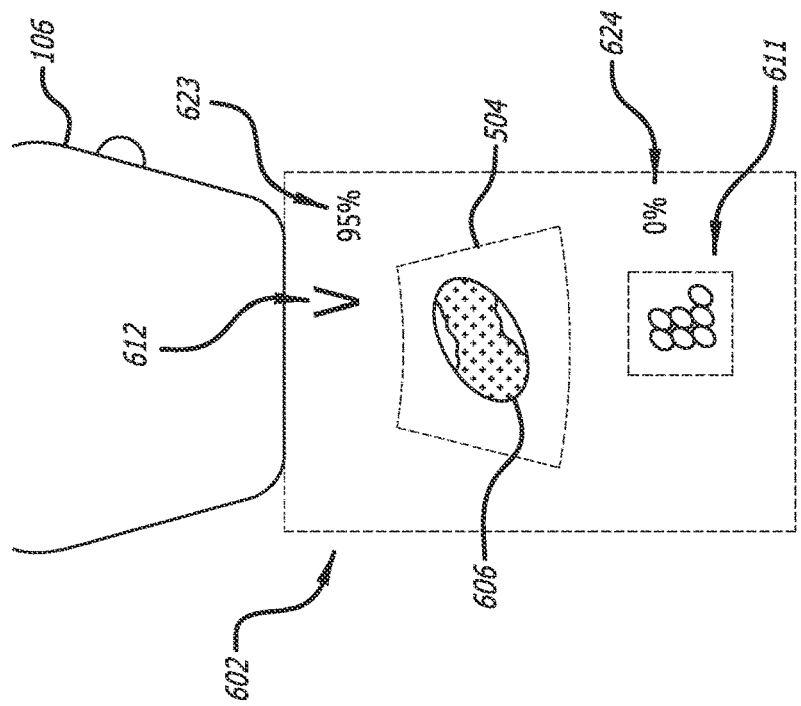
FIG. 6B illustrate the subcutaneous target area of FIG. 6A further illustrating the application of doppler ultrasound in accordance with some embodiments.
Figure 6A:
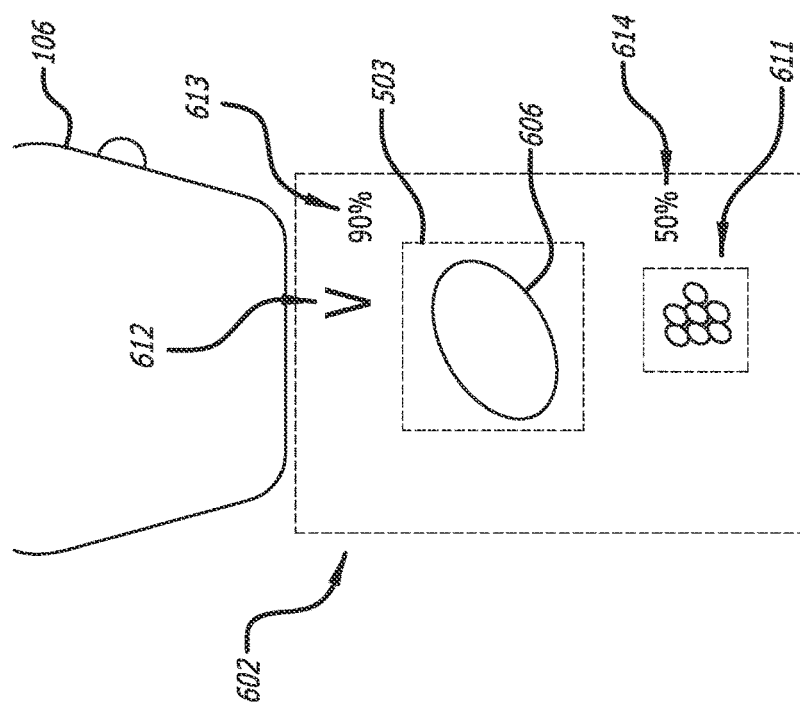
FIG. 6A illustrate another exemplary subcutaneous target area of a patient for ultrasound imaging including a blood vessel and an additional anatomical element in accordance with some embodiments.

FIGS. 6A-6B illustrate a subcutaneous target area of a patient for ultrasound imaging (i.e., for display in an ultrasound image) in accordance with further embodiments of the system 100. Similar to FIGS. 5A-5B, FIGS. 6A-6B illustrate a blood vessel 606 within a predefined target area 602 (i.e., ultrasound image). Further illustrated within the predefined target area 602 in an additional anatomical element 611 shown as a bundle of nerves. However, the anatomical element 611 is not limited to a bundle of nerves. As such, the anatomical element 611 may comprise a bone, a ligament, a tendon, or another blood vessel. In similar fashion, more than one additional anatomical element 611 may be included in the predefined target area 602. As shown in FIGS. 6A-6B notifications may be superimposed atop the ultrasound image when the ultrasound image is portrayed on the display 104. In some embodiments, the notifications include an identity 612 of the blood vessel 606 (e.g., "V" indicating a vein). The notifications further include indications of confidence as further described below. FIG. 6A illustrates a scenario where the identity of the blood vessel 606 is determined without utilizing doppler ultrasound. Conversely, FIG. 6B illustrates a scenario, where determining the identity of the blood vessel 606 includes doppler ultrasound.

In the exemplary instance shown in FIG. 6A, the system 100 has determined that the blood vessel 606 is a vein at a confidence level 613 of 90%. Similarly, the system 100 as determined a confidence level 614 of 50% associated with the anatomical element 611. In other words, as a result of the identity determination, the clinician may understand that the probability that the blood vessel 606 is a vein is 90%. Similarly, the clinician may understand that the probability that the anatomical element 611 is a vein is 50%. In other words, the probability that the anatomical element 611 is a vein is the same as the probability that the anatomical element 611 is not a vein.

Conversely, in the exemplary instance shown in FIG. 6B, the system 100 has determined that the blood vessel 606 is a vein at a confidence level 623 of 95% with doppler ultrasound vs. the confidence level 613 of 90% without doppler ultrasound. Similarly, the system 100 as determined a confidence level 624 of 0% associated with the anatomical element 611 with doppler ultrasound vs. the confidence level 614 of 50% without doppler ultrasound. By way of summary, the utilization of doppler ultrasound when determining the identity of the blood vessel 606 and/or the anatomical element 611 enhances the confidence of the identity determination. As such, when doppler ultrasound is utilized when determining the identity of the blood vessel 606, the clinician may more reliably avoid a blood vessel identification error when performing an intravascular procedure.

Figure 7:
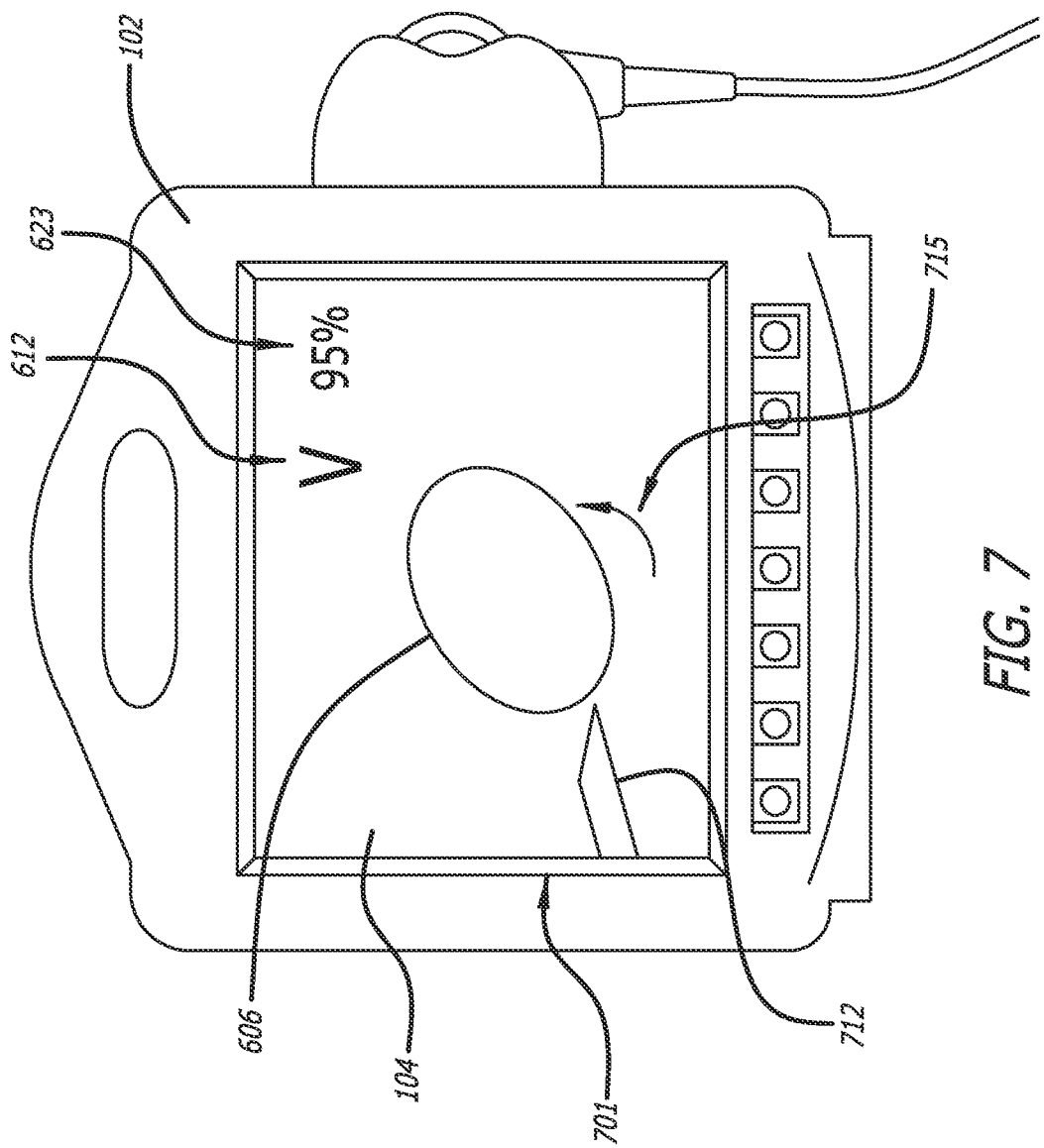
FIG. 7 illustrates a display of the system of FIG. 1 portraying an ultrasound image of a blood vessel in accordance with some embodiments.

FIG. 7 illustrates the console 102 portraying an ultrasound image 701 of the predefined target area on the display screen 104. Depicted in the ultrasound image 701 is the blood vessel 606 (or more specifically an image of the blood vessel 606). Superimposed atop the ultrasound image 701 are the blood vessel identity 612 and the confidence for the identity 623. In some embodiments, a direction indicator 715 of the blood flow direction within the blood vessel 606 may also be superimposed.

In some embodiments, an iconographic representation 712 of the medical device 112 (FIG. 3A) may also be superimposed atop the atop the ultrasound image 701 to assist the clinician in inserting the medical device 112 into the blood vessel 606. In some embodiments, the iconographic representation 712 of the medical device 112 may serve as a pointing device similar to a computer mouse. For example, the clinician may adjust a position and/or orientation of the medical device 112 in relation to the blood vessel 351 (see FIG. 3A) and thereby adjust the position of the iconographic representation 712 with respect to the image of the blood vessel 606. In some embodiments, the clinician may provide input to the logic 120 via the iconographic representation 712 to define the doppler ultrasound window 504 (see FIG. 5B). In some embodiments, the clinical may also select the blood vessel 606 as the blood vessel of interest among other blood vessels (not shown) that may be included in the ultrasound image 701.

Methods

Methods of the foregoing ultrasound-imaging systems include methods implemented in the ultrasound-imaging systems. For example, a method of the ultrasound-imaging system 100 includes a non-transitory CRM (e.g., EEPROM) having the logic 120 stored thereon that causes the ultrasound-imaging system 100 to perform a set of operations for ultrasound imaging when the logic 120 is executed by the processor 116 of the console 102. Any methods disclosed herein comprise one or more steps, actions or operations for performing the described method. The method includes operations (e.g., steps or actions) that may be interchanged with one another. In other words, unless a specific order of the operations is required for proper operation of the embodiment, the order and/or use of specific operations may be modified.

Figure 8:
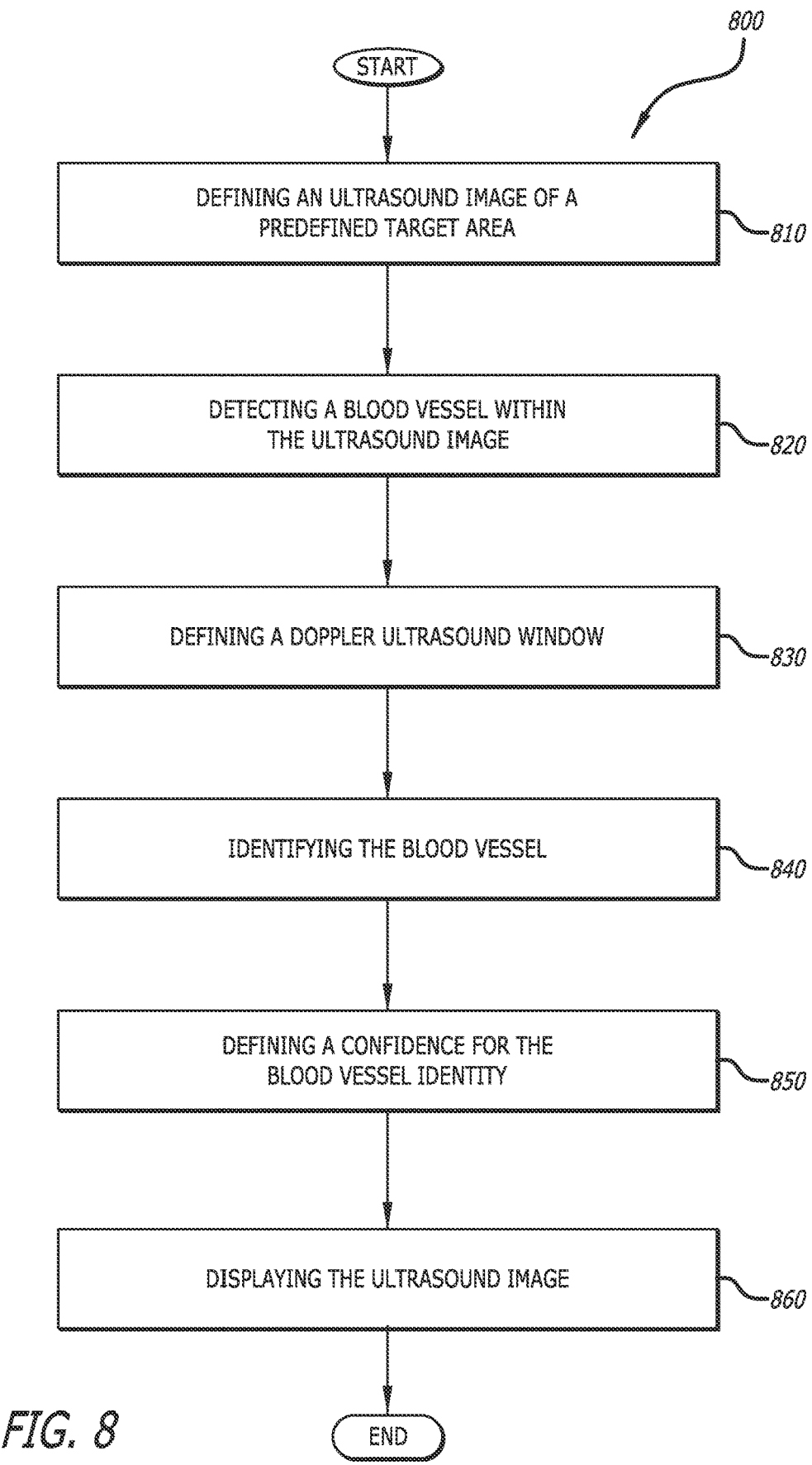
FIG. 8 illustrates a method of system operations that may executed according to system logic in accordance with some embodiments.

FIG. 8 is a flow chart illustrating an exemplary method of the system 100. The method 800 includes operations in accordance with a reference numbers 810-860. Defining the ultrasound image (block 810) may include activating include activating the ultrasonic transducers of the array of the ultrasonic transducers 148 of the ultrasound probe 106 communicatively coupled to the console 102. With the activating operation, the ultrasonic transducers 148 emit generated ultrasound signals into the patient P, receive reflected ultrasound signals from the patient P, and convert the reflected ultrasound signals into corresponding electrical signals for processing into ultrasound images. The activating operations can include activating an approximately linear subset of the ultrasonic transducers 148 of a 2-D array of the ultrasonic transducers 148. Alternatively, the activating operations can include activating a subset of the ultrasonic transducers 148 up to all the ultrasonic transducers 148 in the movable linear array of the ultrasonic transducers 148.

The logic 120 may detect a blood vessel with the ultrasound image (block 820). More specifically, the ultrasound probe may identify color or contrast changes within an ultrasound image that indicate a difference in subcutaneous tissue structure. In some instances, a blood vessel may appear as a black hole in an ultrasound image as defined by ultrasound image data. The ultrasound probe may provide the ultrasound data to the console where the logic 120 may define the black hole as a blood vessel.

The method includes doppler ultrasound operations applied to all or a portion of the ultrasound image. The doppler ultrasound operations including defining a doppler ultrasound window (block 830). The doppler ultrasound window defines a portion of the ultrasound window for assessing motion of elements imaged within the doppler ultrasound window including blood flow within the blood vessel. In some embodiments, the logic 120 may automatically define the doppler ultrasound window to encompass one or more blood vessels upon detection of the one or more blood vessels within the ultrasound image.

In some embodiments, the logic 120 may automatically define the doppler ultrasound window 504 based on the comparison of the ultrasound image with the corresponding ultrasound images stored in memory 118. For example, the corresponding ultrasound images in memory may include a predefined doppler ultrasound window. As such, the logic 120 may define the doppler ultrasound window 504 based on the predefined doppler ultrasound window of the corresponding ultrasound images in memory.

According to further embodiments, the logic 120 may receive an input as may be entered by a clinician via an input device, and the logic 120 may define the doppler ultrasound window based on the input. In other words, the clinician may select a portion of the ultrasound image as the doppler ultrasound window and the logic 120 may define the doppler ultrasound window in accordance with the selection. In some embodiments, the clinician may select a portion of the ultrasound image via the GUI such as with a computer mouse or touch screen. In other embodiments, the clinician may select a portion of the ultrasound image via the control buttons of the ultrasound probe.

In still other embodiments, the clinician may select a portion of the ultrasound image via the medical device. More specifically, the medical device tracking operations may track the medical device with respect to the predefined target area and depict the iconographic representation of the medical device atop the ultrasound image in real time so that the clinician may select the portion of the ultrasound image based on positioning of the medical device.

After detecting a blood vessel, the logic 120 may determine an identity of the blood vessel (block 840). The determination of the identity of the blood vessel may include all or a subset of the logic operations described below. The logic 120 may determine a blood flow condition within the blood vessel by obtaining doppler ultrasound data. The blood flow condition may include a presence or absence of blood flow. The logic 120 may detect, via doppler ultrasound, a blood flow within the blood vessel and thereby further identify the detected black hole to be a blood vessel. The logic 120 may further determine a direction of the blood flow within the blood vessel with respect to the image plane (or more specifically with respect to an orientation of the image plane) and thereby, determine the blood vessel to be a vein or alternatively an artery. The logic 120 may also detect a non-flow condition of the blood vessel (i.e., absence of blood flow), and thereby, determine the blood vessel to be an anatomical element other than a blood vessel, such as a nerve or a bundle of nerves for example.

The operations may include identifying the blood vessel as a vein or an artery based on a blood flow rate or velocity within the blood vessel. The operations may include determining a flow rate (i.e., magnitude of blood flow) with the blood vessel and thereby identify the blood vessel as vein or an artery. For example, in some instances, the blood flow within a defined artery may generally be greater than a blood within an adjacent vein. Accordingly, the logic 120 may obtain a blood flow rate or velocity within a first blood vessel and further obtain a blood flow rate or velocity within a second blood vessel adjacent the first blood vessel. The logic 120 may then compare the determined blood flow rates and identify the blood vessel with the greater flow rate as an artery.

The operations may include identifying the blood vessel as a vein or an artery based on a pulsatility of the blood flow within the blood vessel. The logic 120 may measure, via doppler ultrasound, a pulsatility of the blood flow within the blood vessel. As the arterial blood flow is generally more pulsatile than venous blood flow, the logic 120 may compare a measured pulsatility with a predefined pulsatility limit stored in memory. The logic 120 may thereby determine the blood vessel to be (1) an artery if the measured pulsatility exceeds the pulsatility limit or (2) a vein if the measured pulsatility is less than the pulsatility limit.

In some embodiments, the logic 120 obtain an ECG signal, and determine the pulsatility of the blood flow in coordination with the ECG signal. By so doing, logic 120 may filter out pulse noise within the blood vessel as may be caused by patient movement, patient contact, or other external sources, thereby enhancing an accuracy or reliability of the pulsatility measurement.

In some embodiments, the logic 120 may assess the timing blood flow pulses within blood vessels. More specifically, the logic 120 may determine a timing difference between a blood flow pulse within a first blood vessel and a corresponding blood flow pulse within a second blood vessel based on doppler ultrasound data. Based on the timing difference, the logic 120 may identify one or both of the first blood vessel or the second blood vessel as a vein or as an artery. By way of one example, a blood flow pulse as defined a heartbeat travels along an artery toward an extremity of the patient, such as a hand for example, passing through the predefined target area at a first point in time. The same pulse travels in the opposite direction (i.e., toward the heart) along a corresponding vein, passing back through the predefined target area at a second point in time. The logic 120 determines that the second point in time follows the first point in time by the pulse timing difference. The logic 120 may then determine that the blood flow pulse passing through the predefined target area at the first point in time emanates from an artery, and the blood flow pulse passing through the predefined target area at the second point in time emanates from a vein. In such a way, the logic 120 may identify a blood vessel as an artery or as a vein. In some embodiments, the logic 120 may obtain pulse timing data in coordination with the ECG signal.

In some embodiments, the operations may further include identifying the blood vessel as a vein or an artery based on a spatial positioning of the blood vessel within the ultrasound image. In some embodiments, the logic 120 may compare the ultrasound image with one or more corresponding ultrasound images stored in memory. The logic 120 may more specifically compare the spatial positioning of the blood vessel within the ultrasound image with the spatial positioning of the corresponding blood vessel in the one or more corresponding ultrasound images, where in some embodiments, the spatial positioning includes a subcutaneous depth of the blood vessel. As a result of the comparison, the logic 120 may identify the blood vessel as a vein or alternatively as an artery.

In some embodiments, the operations may further include identifying the blood vessel as a vein or an artery based on a cross-sectional shape of the blood vessel. Typically, a blood pressure within an artery is greater than a blood pressure within a vein. Similarly, the structure of an artery may include a thicker wall than a vein. As such, a cross-sectional shape of the artery may often be rounder than a cross-section shape of a vein. More specifically, the cross-section shape of a vein may be more elliptical, or otherwise elongated, in contrast to the cross-section shape of an artery. In some embodiments, the logic 120 may determine a length and a width of the blood vessel from ultrasound image data. In some, the logic 120 may then determine an aspect ratio of the shape and compare the aspect ratio with an aspect ratio limit stored in memory. As a result of the comparison, the logic 120 may identify the blood vessel as (1) a vein when the aspect ratio exceeds the limit or (2) an artery when the aspect ratio is less than the limit.

The operations may include determining a confidence for the identification of the blood vessel (block 850). The logic 120 may determine the confidence based on all or a subset of the identification operations described above. For example, the logic 120 may determine an individual confidence for each of the identification operations described above and determine a composite confidence for the identification. The confidence determination operation may take several forms. For example, the confidence regarding the identification based on the shape may include assessing a magnitude of difference between the determined aspect ratio and the aspect ratio limit stored in memory. By way of another example, the confidence for the identification based on the blood flow direction within the blood vessel may be greater when the blood flow rate is relatively high vs. relatively low.

The displaying operations further include portraying the ultrasound image on the display screen coupled with the console (block 860). The displaying operations may further include superimposing a visual notification atop the ultrasound image. The notification may indicate the identification of the blood vessel. The notification may also include the confidence where the confidence includes a number (e.g., a percent probability) or other confidence indication such as a low, medium, or high-level indication of confidence.

Other methods may include magnetic signal-related operations. The magnetic signal-related operations can include a converting operation. The converting operation includes converting magnetic signals from a magnetized medical device (e.g., the needle 112) with the magnetic-sensor array 146 of the ultrasound probe 106 into corresponding electrical signals. The processing operations further include processing the corresponding electrical signals of the magnetic signals with the processor 116 into distance and orientation information with respect to the predefined target area so that the iconographic representation of the medical device may be portrayed on the display screen 104.

Other methods may further include a number of optical signal-related operations in combination with further processing and displaying operations. The optical signal-related operations include emitting input optical signals, receiving reflected optical signals, and converting the reflected optical signals into corresponding electrical signals of the optical signals by the optical interrogator 154. The optical signal-related operations also include conveying the input optical signals from the optical interrogator 154 to the number of FBG sensors along the length of the optical-fiber stylet 156, as well as conveying the reflected optical signals from the number of FBG sensors back to the optical interrogator 154 with the optical-fiber stylet 156 disposed in a lumen of the medical device. The processing operation further include processing the corresponding electrical signals of the optical signals with the processor 116 into distance and orientation information with respect to the predefined target area to assist in superimposing the iconographic representation of a medical device on the display screen 104.

Other method operations can include a data-providing operation that includes providing positional-tracking data to the console 102 from the accelerometer 160, the gyroscope 162, the magnetometer 164, or a combination thereof of the ultrasound probe 106 where the tracking data pertains to the position and/or orientation of the ultrasound probe with respect to a trajectory of the one or more blood vessels. Such, operations may enhance an accuracy of the determining of the direction and/or magnitude of blood flow within the one or more blood vessels.

While some particular embodiments have been disclosed herein, and while the particular embodiments have been disclosed in some detail, it is not the intention for the particular embodiments to limit the scope of the concepts provided herein. Additional adaptations and/or modifications can appear to those of ordinary skill in the art, and, in broader aspects, these adaptations and/or modifications are encompassed as well. Accordingly, departures may be made from the particular embodiments disclosed herein without departing from the scope of the concepts provided herein.

What is claimed is:

1. An ultrasound-imaging system, comprising:
   an ultrasound probe including an array of ultrasonic transducers, activated ultrasonic transducers of the array of ultrasonic transducers configured to emit generated ultrasound signals into a patient, receive reflected ultrasound signals from the patient, and convert the reflected ultrasound signals into corresponding electrical signals of the reflected ultrasound signals for processing into ultrasound image data and doppler ultrasound data; and
   a console configured to communicate with the ultrasound probe, the console including one or more processors and a non-transitory computer-readable medium having stored thereon logic that, when executed by the one or more processors, causes operations including:
      obtaining ultrasound image data of a predefined target area of the patient;
      defining an ultrasound image from the ultrasound image data;
      detecting one or more blood vessels within the ultrasound image;
      obtaining doppler ultrasound data pertaining to blood flow within the one or more blood vessels;
      determining a condition of the blood flow based at least partially on doppler ultrasound data; and
      identifying the one or more blood vessels as a vein or alternatively as an artery based at least partially on the condition of the blood flow within the one or more blood vessels,
      wherein:
         determining the condition of the blood flow includes determining a pulse timing difference between a first point in time of a blood flow pulse within a first blood vessel of the one or more blood vessels and a corresponding second point in time of the blood flow pulse within a second blood vessel of the one or more blood vessels based on the doppler ultrasound data; and
         the operations further include identifying (i) the first blood vessel as a vein, and (ii) the second blood vessel as an artery based at least partially on the pulse timing difference.

2. The ultrasound-imaging system of claim 1, wherein determining the condition includes determining a direction of the blood flow within the one or more blood vessels based on doppler ultrasound data, the direction determined with respect to an image plane of the ultrasound image, the operations further including identifying the one or more blood vessels based at least partially on the direction of the blood flow.

3. The ultrasound-imaging system of claim 1, wherein determining the condition includes determining a magnitude of the blood flow within the one or more blood vessels based on doppler ultrasound data, the operations further including identifying the one or more blood vessels based at least partially on the magnitude of the blood flow.

4. The ultrasound-imaging system of claim 1, wherein determining the condition includes determining a pulsatility of the blood flow within the one or more blood vessels based on doppler ultrasound data, the operations further including:
   comparing the pulsatility with a pulsatility limit stored in memory; and
   as a result of the comparing, further at least partially identifying the one or more blood vessels (i) as an artery when the pulsatility exceeds the pulsatility limit or (ii) as a vein when the pulsatility is less than the pulsatility limit.

5. The ultrasound-imaging system of claim 4, wherein:
   the ultrasound-imaging system is configured to obtain an ECG signal from the patient via an ECG monitor coupled with the console, and
   the operations further include determining the pulsatility of the blood flow in coordination with the ECG signal.

6. The ultrasound-imaging system of claim 1, wherein the operations further include:
   determining a cross-sectional shape of the one or more blood vessels based on ultrasound image data; and
   further identifying the one or more blood vessels as a vein or an artery based at least partially on the cross-sectional shape.

7. The ultrasound-imaging system of claim 6, wherein identifying the one or more blood vessels based on the cross-sectional shape includes:
   comparing the cross-sectional shape of the one or more blood vessels with an elliptical shape limit stored in memory, and
   as a result of the comparing, identifying the one or more blood vessels (i) as an artery when the cross-sectional shape is less than the elliptical shape limit or (ii) as a vein when the cross-sectional shape exceeds the elliptical shape limit.

8. The ultrasound-imaging system of claim 1, wherein the operations further include determining a confidence for the identification of the one or more blood vessels based on one or more of:
   a direction of the blood flow,
   a magnitude of the blood flow,
   a pulsatility of the blood flow,
   the pulse timing difference of the blood flow, or
   a cross-sectional shape.

9. The ultrasound-imaging system of claim 1, wherein:
   the operations further include defining a doppler ultrasound window extending at least partially across the ultrasound image, the doppler ultrasound window defines a portion of the ultrasound image for obtaining doppler ultrasound data, and the doppler ultrasound window encompasses the one or more blood vessels.

10. The ultrasound-imaging system of claim 9, wherein defining the doppler ultrasound window includes automatically defining the doppler ultrasound window upon detecting the one or more blood vessels.

11. The ultrasound-imaging system of claim 9, wherein defining the doppler ultrasound window includes:

receiving an input via an input device of the ultrasound-imaging system; and defining the doppler ultrasound window based on the input, the input including a selected portion of the ultrasound image.

12. The ultrasound-imaging system of claim 11, wherein the input device includes a graphical user interface of a display.

13. The ultrasound-imaging system of claim 11, wherein the input device includes control buttons of the ultrasound probe.

14. The ultrasound-imaging system of claim 9, wherein the ultrasound probe further includes an array of magnetic sensors configured to convert magnetic signals from a magnetized medical device including a needle into corresponding electrical signals of the magnetic signals for processing by the one or more processor into at least one of position information and orientation information of the magnetized medical device with respect to the predefined target area.

15. The ultrasound-imaging system of claim 14, wherein the operations further include superimposing an iconographic representation of the magnetized medical device atop the ultrasound image.

16. The ultrasound-imaging system of claim 15, wherein the operations further include defining the doppler ultrasound window based on at least one of a position or an orientation of the iconographic representation of the magnetized medical device atop the ultrasound image.

17. The ultrasound-imaging system of claim 15, wherein the operations further include selecting a blood vessel of interest from the one or more blood vessels based on at least one of a position and an orientation of the iconographic representation of the magnetized medical device atop the ultrasound image.

18. The ultrasound-imaging system of claim 1, the ultrasound probe further including: an accelerometer, a gyroscope, a magnetometer, or a combination thereof configured to provide tracking data to the console, the tracking data pertaining to at least one of a position and an orientation of the ultrasound probe with respect to a trajectory of the one or more blood vessels, wherein the operations further include processing the tracking data in combination with obtaining the doppler ultrasound data to enhance an accuracy of determining of at least one of a direction or a magnitude of blood flow within the one or more blood vessels.

19. The ultrasound-imaging system of claim 1, wherein the operations further include:

portraying the ultrasound image on a display of the system; and superimposing a notification atop the ultrasound image, the notification including the identification of the blood vessel.

20. The ultrasound-imaging system of claim 19, wherein the notification further includes a confidence for the identification of the one or more blood vessels.

* * * * *